US011135589B2

United States Patent
Bhansali et al.

(10) Patent No.: US 11,135,589 B2
(45) Date of Patent: Oct. 5, 2021

(54) LARGE MICROFLUIDIC BIOREACTOR AND MANUFACTURING METHOD THEREOF

(71) Applicants: Shekhar Bhansali, Weston, FL (US); Maximiliano S. Perez, Miami, FL (US); Betiana Lerner, Miami, FL (US); Natalia Bourguignon, Miami, FL (US)

(72) Inventors: Shekhar Bhansali, Weston, FL (US); Maximiliano S. Perez, Miami, FL (US); Betiana Lerner, Miami, FL (US); Natalia Bourguignon, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 17/130,531

(22) Filed: Dec. 22, 2020

(65) Prior Publication Data

US 2021/0129151 A1     May 6, 2021

Related U.S. Application Data

(62) Division of application No. 16/573,450, filed on Sep. 17, 2019, now Pat. No. 10,926,261.

(51) Int. Cl.
*B01L 3/00* (2006.01)
*C08L 33/12* (2006.01)
(Continued)

(52) U.S. Cl.
CPC ... *B01L 3/502792* (2013.01); *B01L 3/502707* (2013.01); *B29C 35/02* (2013.01); *B81C 1/00119* (2013.01); *C08L 33/12* (2013.01);

*C08L 51/085* (2013.01); *C12M 23/16* (2013.01); *B01L 2200/027* (2013.01);
(Continued)

(58) Field of Classification Search
CPC ......... B01L 3/502792; B01L 3/502707; B01L 2200/027; B01L 2300/123; B01L 2300/0832; B29C 35/02; B81C 1/00119; B29L 2007/00; C08L 51/085; C12M 23/16; G03F 7/40; G03F 7/0017; G03F 7/2022

See application file for complete search history.

(56) References Cited

U.S. PATENT DOCUMENTS

2005/0227182 A1    10/2005   Ali
2010/0216241 A1*   8/2010    Yu .......................... C12M 23/16
                                                                          435/395

(Continued)

OTHER PUBLICATIONS

Adam Selsman, Replica Molding (REM), Mar. 24, 2017, https://openwetware.org/wiki/Replica-molding(REM)—Adam Selsman (Year: 2017).

*Primary Examiner* — Michael L Hobbs
(74) *Attorney, Agent, or Firm* — Saliwanchik, Lloyd & Eisenschenk

(57) ABSTRACT

Large bioreactors based on microfluidic technology, and methods of manufacturing the same, are provided, The big microbioreactor can include a chip or substrate having the microfluidic channels thereon, and the chip can be manufactured by forming a master mold, forming a male mold from a photopolymer plate using replica molding with the Fmold, and transferring features of the male to a polymer material.

18 Claims, 23 Drawing Sheets

(51) Int. Cl.
    *C08L 51/08*    (2006.01)
    *B29C 35/02*    (2006.01)
    *C12M 3/06*     (2006.01)
    *B81C 1/00*     (2006.01)
    *B29L 7/00*         (2006.01)
    *G03F 7/00*         (2006.01)
    *G03F 7/40*         (2006.01)
    *G03F 7/20*         (2006.01)

(52) U.S. Cl.
    CPC . *B01L 2300/0832* (2013.01); *B01L 2300/123* (2013.01); *B29L 2007/00* (2013.01); *G03F 7/0017* (2013.01); *G03F 7/2022* (2013.01); *G03F 7/40* (2013.01)

(56) References Cited

U.S. PATENT DOCUMENTS

| | | |
|---|---|---|
| 2011/0192233 A1 | 8/2011 | Aizenberg |
| 2012/0034695 A1 | 2/2012 | Sethu |
| 2015/0273735 A1* | 10/2015 | Cohen ............... B32B 37/182 422/501 |
| 2018/0355298 A1 | 12/2018 | Loskill |
| 2020/0056142 A1 | 2/2020 | Masaeli |

* cited by examiner

LARGE MICROFLUIDIC BIOREACTOR AND MANUFACTURING METHOD THEREOF

CROSS-REFERENCE TO A RELATED APPLICATION

The present application is a divisional application of U.S. patent application Ser. No. 16/573,450, filed Sep. 17, 2019, now U.S. Pat. No. 10,926,261, issued Feb. 23, 2021, the disclosure of which is hereby incorporated by reference in its entirety, including all figures, tables, or drawings.

BACKGROUND

Polydimethylsiloxane (PDMS) is a widely used material in the manufacture of microfluidic devices because this transparent elastomer offers chemical resistance and biocompatibility. PDMS devices are easy to fabricate and enable a wide range of applications. PDMS microdevices are mostly fabricated via soft lithography technology, with SU-8 being the most common photoresist used for this purpose. This technique allows the creation of microstructures with high resolution (~1 μm), but it has several significant disadvantages. The molds normally use silicon wafers as substrates, but such substrates are fragile with limited size (normally not wider than 4 inches or 6 inches) and the photoresin is prone to delamination. In addition, SU-8 mold fabrication requires clean room facilities, which are not available in all countries, limiting their use only to laboratories that have access to expensive equipment to generate the masks and perform the lithographic processes.

The increase of lab on a chip (LOC) applications in various research fields brings the opportunity to develop new low-cost and high feasibility methodologies for PDMS microdevice fabrication. Some alternative fabrication techniques do not require lithography, such as thermo-plastic building blocks, toner transfer masking, and laser swelling. However, existing techniques that do not use lithography do not achieve the resolution of photoresins and/or the processes are extremely expensive.

BRIEF SUMMARY

Embodiments of the subject invention provide novel and advantageous bioreactors, based on microfluidic technology, that are large (e.g., centimeter-scale) overall while having microfluidic channels, as well as method of manufacturing the same and methods of using the same. A big microbioreactor (BM bioreactor) is a microfluidic-based bioreactor of large size (e.g., at least a few centimeters wide and/or long), which does not exist in the related art and can be applied in several fields, including the private sector and the academic sector. Optimizing one or more of the variables of medium flow velocity, average dilution speed, and aeration (possibly among other parameters), can provide effective control of the cellular growth in the BM bioreactor while at the same time maintaining the target metabolic activity of the cell culture. The BM bioreactor can include a chip or substrate having the microfluidic channels thereon, and the chip (which can be referred to as a "big chip") can be manufactured using, for example, a mold made of any photopolymeric printing plate through a novel method.

In an embodiment, a method of manufacturing a macro-sized microbioreactor (BM bioreactor) having an arrangement of microfluidic channels can comprise: forming a master mold (Fmold) having a design corresponding to the arrangement of microfluidic channels; forming a male mold (ERmold) from a photopolymer plate, using replica molding with the Fmold; and transferring features of the ERmold to a polymer material to give the BM bioreactor having the arrangement of microfluidic channels. The arrangement of microfluidic channels can have an area of at least 1 square inch ($in^2$) (e.g., at least 20 $in^2$).

In another embodiment, a macro-sized microbioreactor (BM bioreactor) can comprise a plurality of microfluidic channels, and an area of the BM bioreactor taken up by the plurality of microfluidic channels can be at least 1 $in^2$ (e.g., at least 20 $in^2$).

BRIEF DESCRIPTION OF THE DRAWINGS

FIG. 14A is for a UVA exposure time of 35 s on the reverse side; FIG. 14B is for a UVA exposure time of 40 s on the reverse side; and FIG. 14C is for a UVA exposure time of 48 s on the reverse side.

DETAILED DESCRIPTION

Figure 1:
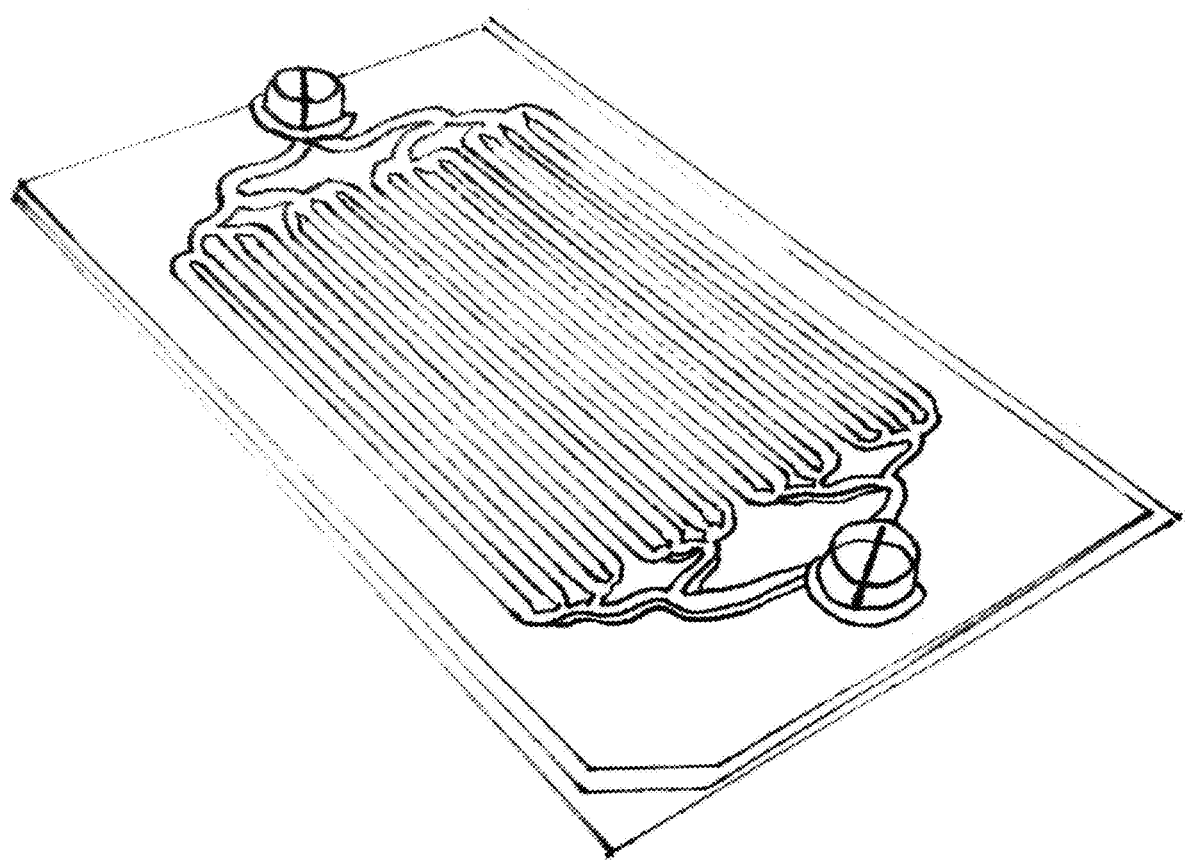
FIG. 1 is an image of a big microfluidic (BM) bioreactor, according to an embodiment of the subject invention. A United States penny (diameter of about 19 millimeters) is shown at the bottom center of the image to provide a size reference for the BM bioreactor.

Embodiments of the subject invention provide novel and advantageous bioreactors, based on microfluidic technology, that are large (e.g., centimeter-scale) overall while having microfluidic channels, as well as method of manufacturing the same and methods of using the same. A big microbioreactor (BM bioreactor) is a microfluidic-based bioreactor of large size (e.g., at least a few centimeters wide and/or long), which does not exist in the related art and can be applied in several fields, including the private sector and the academic sector. Optimizing one or more of the variables of medium flow velocity, average dilution speed, and aeration (possibly among other parameters), can provide effective control of the cellular growth in the BM bioreactor while at the same time maintaining the target metabolic activity of the cell culture. The BM bioreactor can include a chip or substrate having the microfluidic channels thereon, and the chip (which can be referred to as a "big chip") can be manufactured using, for example, a mold made of any photopolymeric printing plate through a novel method.

Related art microbioreactors based on microfluidic technology typically provide a microenvironment and growth conditions better than those related art bioreactors produced on a large scale. Microbioreactors based on microfluidic technology in general allow for application as scale reduction models and are frequently used in research and development (R&D) laboratories. Microbioreactors are typically very small (μm-scale or mm-scale).

BM bioreactors of embodiments of the subject invention can be formed of any suitable material known in the art. Polydimethylsiloxane (PDMS) is discussed extensively herein as a material used to form BM bioreactors, but this is for exemplary purposes only and should not be construed as limiting. In an embodiment, a method of fabricating a BM bioreactor can include three main steps: (1) fabrication of a photopolymer flexographic master mold (which can be referred to as "Fmold"); (2) manufacture of a reusable epoxy resin male mold (which can be referred to as "ERmold") from the Fmold by replica molding; and (3) transfer of the ERmold features to the polymer material of the BM bioreactor (e.g., PDMS). These steps are discussed in more detail below, and it is noted that in some embodiments, BM bioreactors can be designed using software (e.g., Layout Editor software).

In an embodiment, a method of manufacturing a BM bioreactor can include preparing an Fmold by the following steps: designing a microchannel network; transferring the design to a film (e.g., a thermal imaging film); laminating the film onto an unexposed photopolymer (e.g., a photopolymer plate); exposing a bottom (or reverse) side of the photopolymer to radiation (e.g., UV radiation, such as UVA radiation); exposing a top (or front) side of the photopolymer (that is opposite from the bottom side) to radiation (e.g., UV radiation, such as UVA radiation); removing the film; washing the photopolymer; drying the washed photopolymer (e.g., with ambient air, with warm air, or in an oven); and exposing the top side of the dried photopolymer to radiation (e.g., UV radiation, such as UVA and/or UVC radiation). The method can further include: heating the Fmold (e.g., in an oven) after the radiation exposure of the dried photopolymer; treating the Fmold in a vacuum chamber; and/or cleaning the Fmold (e.g., in a solution in an ultrasonic bath), which can be followed by drying and cleaning in a gas stream (e.g., a nitrogen stream). The transferring of the design to the film can be done by, for example, imaging of the film with a laser (e.g., an infrared laser). Each of the exposure steps can be done at a desired, predetermined energy and/or for a desired, predetermined amount of time. Each of the drying steps can be done at a desired, predetermined temperature and/or for a desired, predetermined amount of time.

In an embodiment, a method of manufacturing a BM bioreactor can include preparing an ERmold by the following steps: mixing a first material (e.g., a resin such as an epoxy resin) and a second material (e.g., a curing agent) (e.g., by hand-stirring for a predetermined amount of time and at a predetermined weight ratio of the first and second materials (e.g., 2:1)); ultrasonically treating the mixture (e.g., using a bath-type sonicator for a predetermined amount of time to remove air bubbles); disposing (e.g., pouring) the mixture onto the Fmold; curing the mixture (e.g., at a predetermined temperature for a predetermined amount of time); and peeling the cured mixture off the Fmold to form the male ERmold.

In an embodiment, a method of manufacturing a BM bioreactor can include preparing transferring the ERmold features to a polymer by the following steps: mixing the polymer (e.g., PDMS) with a curing agent (e.g., at a predetermined ratio, such as 10:1); optionally removing any air bubbles (e.g., by placing the polymer and curing agent mixture under vacuum); disposing (e.g., pouring) the polymer and curing agent mixture on the ERmold; curing the polymer and curing agent mixture (e.g., at a predetermined temperature for a predetermined amount of time); peeling off the cured polymer from the ERmold and optionally cutting as needed to give the channel portion of the BM bioreactor. Fluidic connections can be punched (e.g., with a hollow punch, with a desired, predetermined an inner diameter). The method can further include bonding (e.g., irreversibly bonding) the polymer device to a rigid substrate (e.g., a glass substrate); and/or exposing the polymer device to a high-frequency generator for a predetermined amount of time. Catheters and/or hoses (e.g., stainless steel catheters and/or hoses) can be connected at the inlet and/or outlet channels. Syringes can also be included with the catheters and/or hoses.

Figure 4:
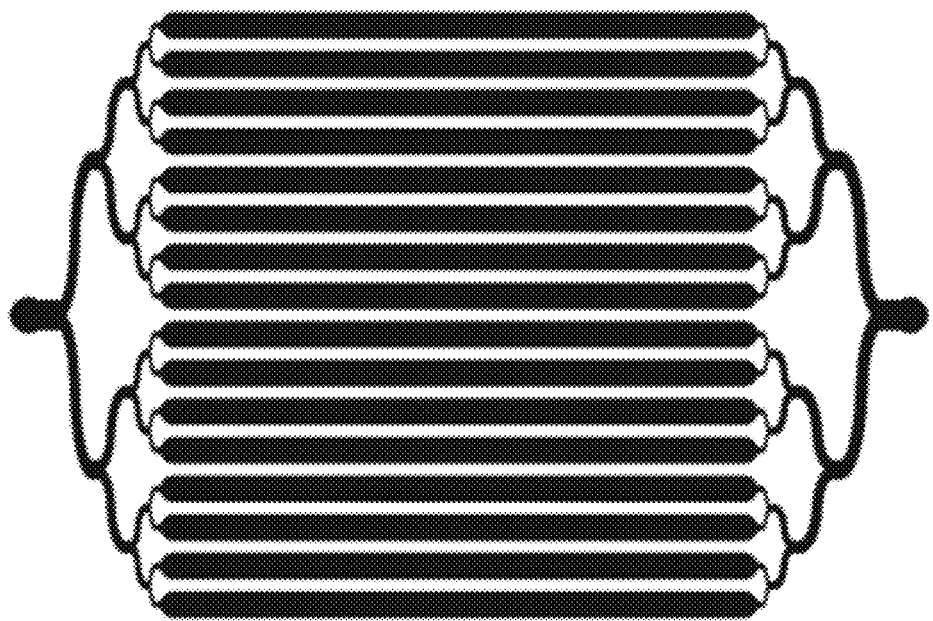
FIG. 4 is a top view of the channels of a BM bioreactor, according to an embodiment of the subject invention. The dark portions are channels.
Figure 21:
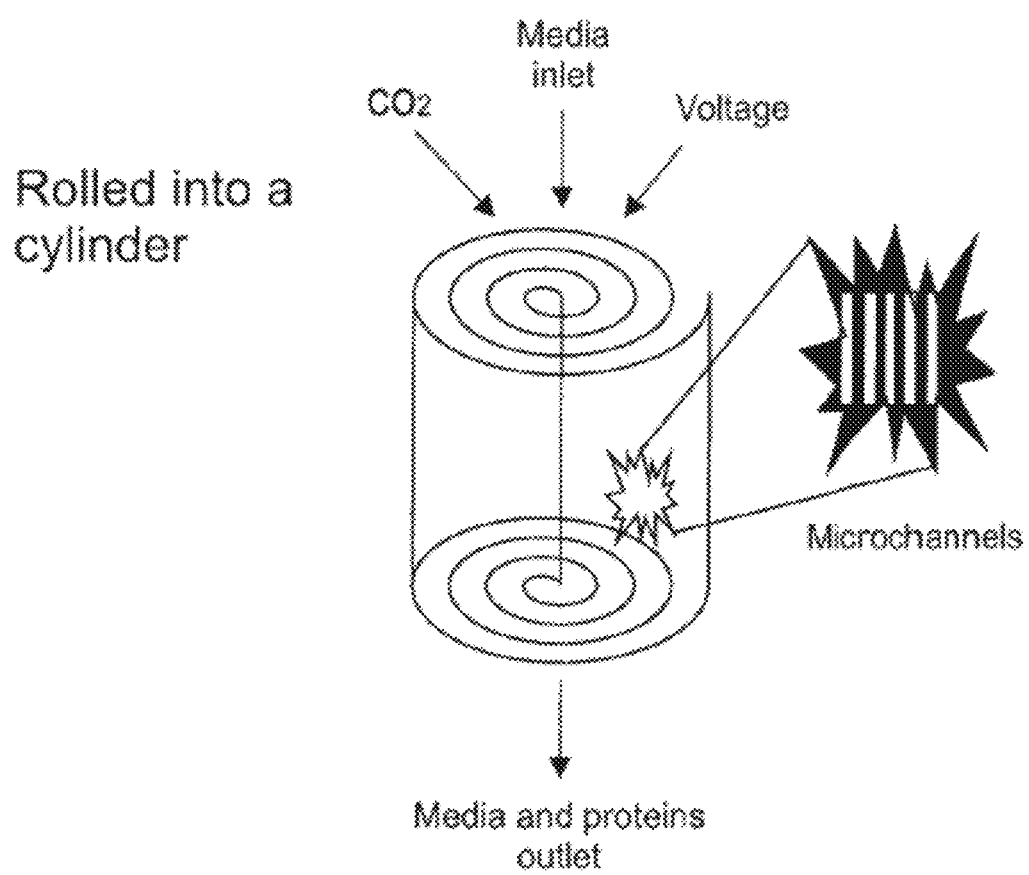
FIG. 21 is a schematic view of a rolled BM bioreactor, according to an embodiment of the subject invention.
Figure 22:
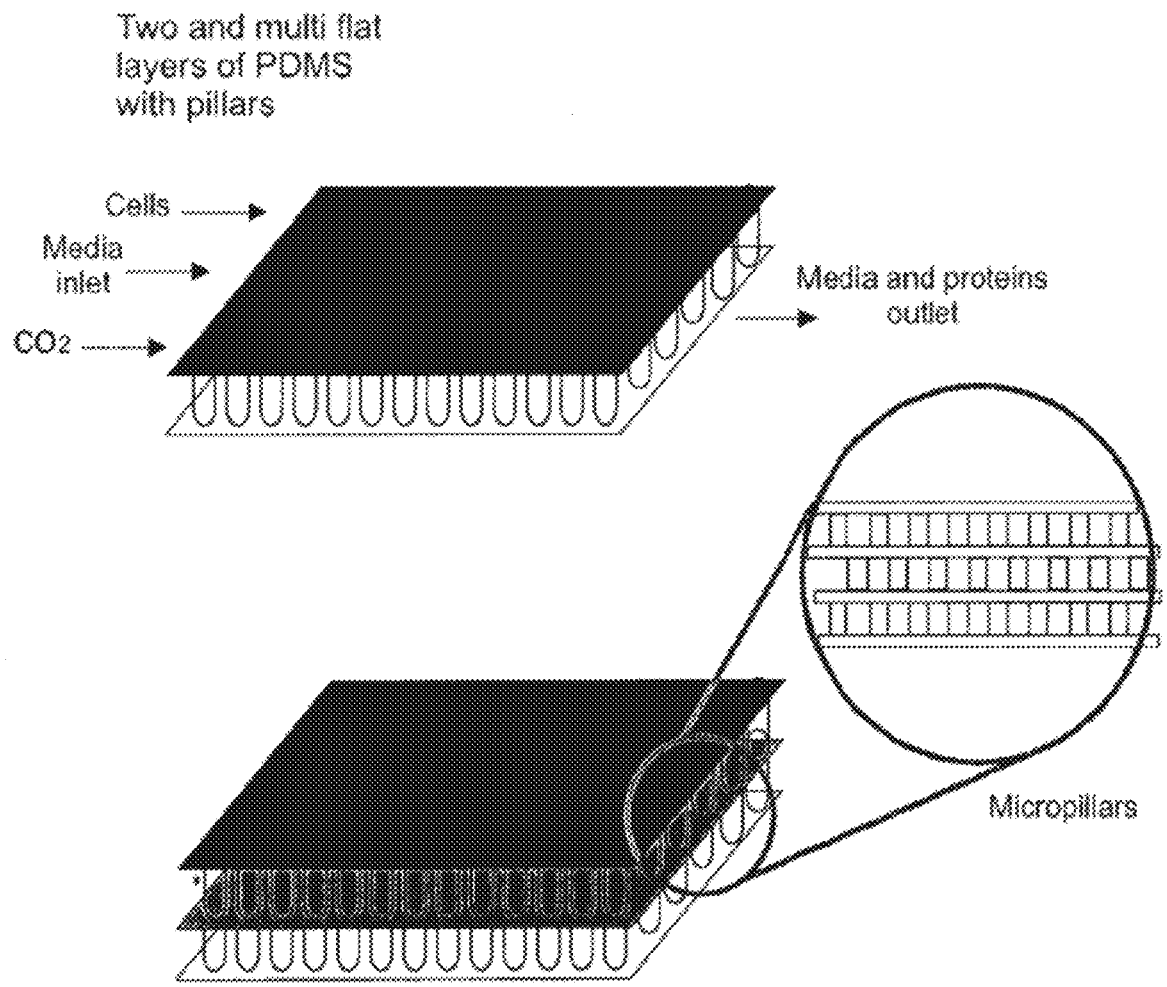
FIG. 22 is a schematic view of a single layer BM bioreactor (top portion), and a multi-layer BM bioreactor (bottom portion), according to embodiments of the subject invention.
Figure 23:
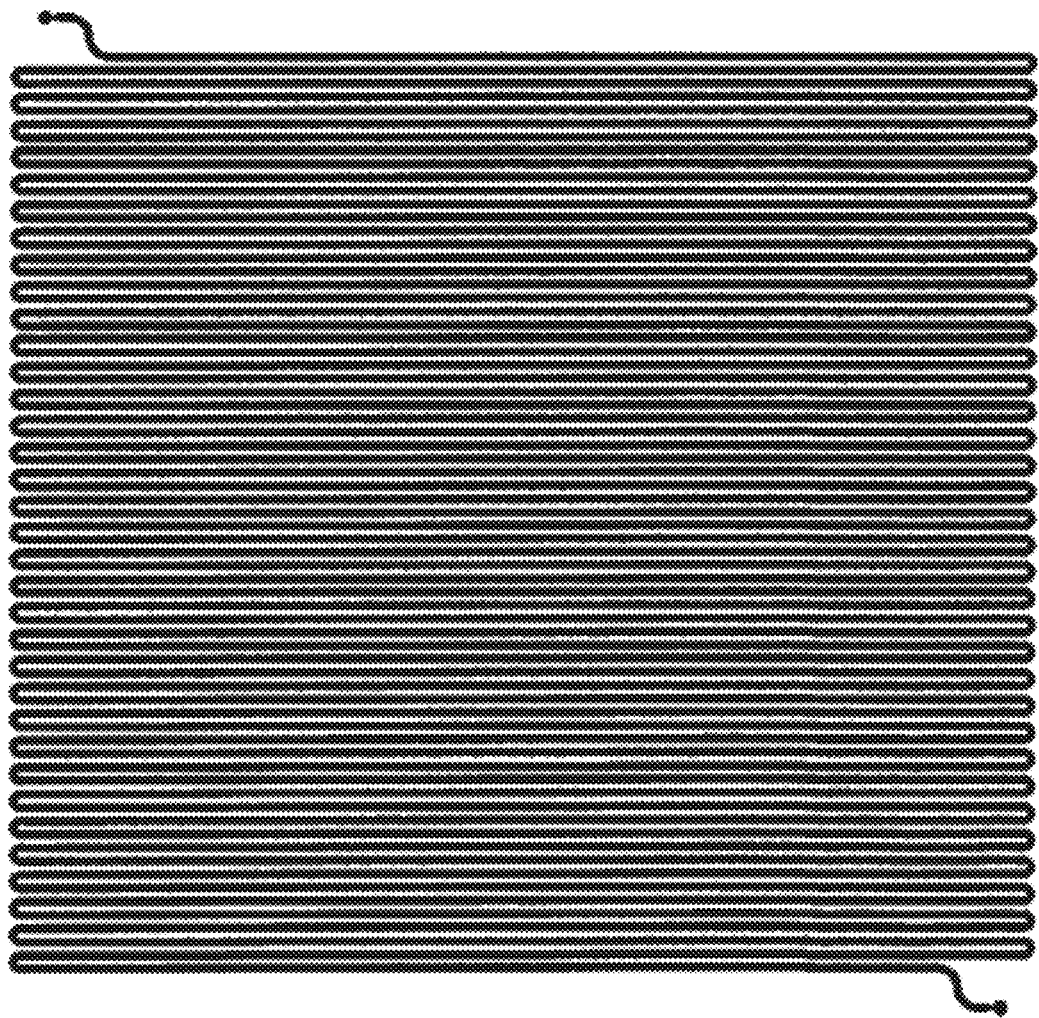
FIG. 23 is a top view of the channels of a BM bioreactor, according to an embodiment of the subject invention. The dark portions are channels.

BM bioreactors of embodiments of the subject invention can be manufactured with different designs, including but not limited to being rolled into a cylinder, having two flat layers of polymer (e.g., PDMS) with pillars, being a chip with normal channels in different arrangements, and having stacked layers of chips. They can be of different sizes depending on the desired purpose/design and can be, for example 1 meter×2 meters). FIG. 4 shows a top view of the channels of a BM bioreactor; FIG. 21 shows a schematic view of a rolled BM bioreactor; FIG. 22 shows a schematic view of a single layer BM bioreactor (top portion), and a multi-layer BM bioreactor (bottom portion); and FIG. 23 shows a top view of the channels of a BM bioreactor. These show non-limiting examples of different types of BM bioreactors of embodiments of the subject invention. It is possible to cultivate all types of organisms in the BM bioreactor, with adherent and non-adherent cells such as mammalian cells, bacteria, and fungi.

Referring to FIG. 4, the design can include an inlet and an outlet, and can also include one or more tanks where the cell culture can be carried out. The number and width of the cisterns can vary according to the final size of the bioreactor. From the inlet and outlet to the cisterns there is a network of symmetrical microchannels with curved corners and different channel widths according to the level that allow a uniform flow in and out. The design can be made using any suitable material, including but not limited to PDMS, poly methyl methacrylate (PMMA), or glass.

Referring to FIG. 23, the serpentine design can include a single channel with an inlet and an outlet that runs through the entire microbioreactor area. This design provides longer cell retention time. The width and height of the channel can vary according to the needs of the specific application. The design can be made using any suitable material, including but not limited to PDMS, PMMA, or glass.

Referring to FIG. 21, the design that is rolled into a cylinder can be formed by a layer of microchannels arranged in a sheet that winds itself in this way to increase the area of the microbioreactor. It has an inlet and an outlet at the top and bottom of the cylinder (the top can be inlet or outlet, as desired, and the same is true for the bottom). The design can be made using any suitable material, including but not limited to PDMS, PMMA, or glass.

Referring to FIG. 22, two or more flat layers of polymer (e.g., PDMS) with micro-pillars (separated by, for example, 200 μm) can give a height in microns that allows the bioreactor to have laminar flow in each layer where the cell cultures will be carried out. By increasing the layers, an increase in volume and area can be obtained. The design can be made using any suitable material, including but not limited to PDMS, PMMA, or glass.

Embodiments of the subject invention provide BM bioreactors, or "big chips" that are bioreactors based on microfluidics. Microfluidic lab on a chip (LOC)-type devices are an emerging and innovative technology that offers advantages such as short response time of the process, high surface area/volume ratio, and a homogeneous and controllable microenvironment, which would be associated with a significant reduction in development costs and increase in the quality of the bio-product obtained. Conventional microfluidic bioreactors are not bigger than the wafer size, but embodiments of the subject invention address the problem of small bioreactors by producing large chips that are still based on microfluidics. BM bioreactors of embodiments of the subject invention can have a surface area (of the upper surface having the microfluidic channels thereon) in a range of, for example, 1 square inch ($in^2$) to 21 square feet ($ft^2$), though embodiments are not limited thereto. In the big chip, the laminar flow condition and same advantages from smaller traditional chips are maintained, allowing an increase production, better process control, less cell stress, ability to produce continuously, easy system management, and the possibility of optimization to improve performance. The use of an appropriate combination of medium flow, average dilution rate, and aeration, among other parameters, allows for effective control of cellular retention and growth in the big chip while at the same time maintaining the metabolic activity of the cell culture. No related art microdevice provides such advantages.

Conventional methods for the development of bioprocesses use extensive experiments in laboratory scale to select the best conditions of cellular metabolism and/or to obtain products. These selection processes require a large number of samples, time of experimentation and chemical analysis, and generation of waste, and are not capable of performing parallel tests, unlike microbioreactors. Therefore, the use of BM bioreactors of the embodiments of the subject invention accelerates the steps of bioprocess research and increases productivity on a large scale as well. In the BM bioreactor the growth of the two cell morphologies is possible, among other compared to hollow fiber reactors, because it reaches a large volume (e.g., 2000 ml or more). The laminar flow allows better oxygenation and behavior of the cells, so it is possible to see the physiological state of the cell, and monitoring in real time all parameters of the BM bioreactor decreases manufacturing costs.

In addition to the increase in size compared to traditional chips, BM bioreactors of the embodiments of the subject invention can be prepared in many different configurations, including but not limited to rolled into a cylinder, two flat layers with pillars, chips with normal channels in different arrangements, and stacked layers of chips (see, e.g., FIGS. 4 and 21-23).

Manufacturing methods of embodiments of the subject invention can be based on a photopolymer (e.g., a commercially available photopolymer) that is independent of clean room conditions and the use of a resin that are part of the conventional mold manufacturing process for microfluidics. BM bioreactors of, e.g., up to 21 ft$^2$ can be fabricated while preserving all the properties of small microdevices. Also, in comparison with related art fabrication methods for microfluidic devices using photolithography (SU-8 resin), manufacturing methods of embodiments of the subject invention shows many advantages, including but not necessarily limited to the following.

(i) The flexographic plate is not prone to delamination because it is not a polymer deposited on a wafer, as in related art methods. The mold can be formed of a polymer as a whole, so its useful life can be tens or hundreds of times greater.

(ii) The process is more economical than related art methods.

(iii) The patterns of the mold can be obtained directly from the pre-established software, so a glass or quartz mask for photolithography is not necessary.

(iv) Molds of dimensions much greater than those achieved with SU-8 or other resins on silicon wafers can be achieved.

(v) Spin coating that is used in related art methods is not necessary (vi) In related art methods, the resin is deposited on a substrate (usually a silicon wafer) to generate the mold, but in methods of embodiments of the subject invention, the polymer can be the mold (i.e., a separate substrate is not required and can be omitted)

(vii) Methods of embodiments of the subject invention allow for the generation of different heights in the same mold, by only changing the UV exposure time in different areas of the mold. In related art methods this is achieved through a laborious process including successive stages of spin coating, exposure, and development. The control of the height of the structures obtained by SU-8 is made by varying the characteristics of the resin (viii) The spin-coating process can be omitted. Because multiple levels can be obtained from the same polymer, it is not necessary to add additional compounds or perform subsequent procedures.

(iv) The control of the height of the devices can be accomplished by varying the exposure times. Keeping the initial polymer constant, a first stage of UVA development can be done, and then a mask that blocks certain spaces of the mold can be placed and subsequently another UVA development stage can be performed. Blocking certain areas of the mold prevents or inhibits further degradation of the polymer, thus generating multiple levels or "multilevels".

Methods of embodiments of the subject invention allow for the production of multiple microdevices with different height characteristics without generating higher costs or manufacturing times. To make multiple microdevices, the areas for which UVA exposure is not desired are blocked and then the development process is carried out on the entire polymer sheet. The use of a photopolymer in the manufacture of microfluidic chips has not been done in related art methods.

BM bioreactors of embodiments of the subject invention show great versatility in their use, and designs can be used, developed, and/or optimized according to the need of a user's biomanufacturing process. Sensors to measure pH, temperature, $O_2$ concentration, $CO_2$, and/or other parameters (e.g., other parameters that may be useful and/or necessary based on the biological process to be performed) can be incorporated into the BM bioreactor.

BM bioreactors of embodiments of the subject invention provide a macro-sized microdevice that can accelerate the bioprocess, increase the efficiency, provide more yield with a significant reduction in development costs, and increase the quality of the bio-product obtained. A BM bioreactor based in microfluidic technology working at laminar flow condition provides a controlled microenvironment and optimized conditions to perform bioprocesses. Such BM bioreactors can provide shorter response time of the process, high surface area/volume ratio, homogeneous and controllable cell physiological conditions, continuous manufacturing, and a decrease in overall physical space used. A microfluidic device on a macro-scale can be used as a bioreactor for the production of biomass or bio-products of biotechnological interest. The BM bioreactor can automate and reduce the operations of a biotechnological production line to a confined space. In this way, the devices and methods of embodiments of the subject invention can replace traditional macroscale methods that consume more reagents and time.

Microbioreactors based on microfluidics aim to provide a microenvironment and conditions similar to those produced on a large scale, which allows their application as scale reduction models. They are gaining more ground in the market of R&D laboratories, with the most common applications being the selection of strains and the optimization of the medium and culture conditions. Specifically, concentration gradient generators, microfluidics based on microdroplets and microbioreactors, are explored as useful tools that can contribute to industrial biotechnology. These tools present potential applications, including as commercial platforms to optimize the development of bioprocesses such as cell screening, encapsulation of biocatalysts, and determination of critical kinetic parameters. The advantage of microbioreactors is that a large number of cultures can be developed in a limited and reduced space within the laboratory, thereby resulting in a faster process development and a shorter time to go to market. It also provides the opportunity for individual or multiple cell analysis with localized and high resolution experimental applications under dynamic conditions. Because microfluidics is a young discipline that is experiencing a high growth rate based on the discovery of its applications both in research and in industry to improve life of people, so embodiments of the subject invention provide many advantages in both the academic and industrial sectors (e.g., pharmaceutical, biotechnology, oil and gas).

Methods of embodiments of the subject invention provide a good alternative to related art microfluidic manufacture methods that use photoresin over silicon wafers. The fidelity of replication, stability, and durability of the Fmold have been demonstrated (see Examples 4 and 5 below). It can be used multiple times with the acquisition of reliable replicas, without delamination, because the mold and the structures designed can give a unique piece. This method allows the manufacture of microfluidic molds achieving very large dimensions (e.g., 1270×2062 $mm^2$ or larger), reaching a minimum structure size of 25 µm and structure height in a range of, for example, from 53 µm to 1500 µm. No known related art method gives these advantageous characteristics. The use of the Fmold for the manufacture of microfluidic devices allows the integration of multiple laboratory functions and detection systems in a single layer. Another advantage is that the Fmolds can be commercially obtained at much lower cost than SU-8 molds. In addition, because Flexcel technology is commonly used in the graphics industry, Fmolds can be acquired worldwide. The methods of embodiments of the subject invention can help a positive evolution in the microfluidic field, serving as support for many laboratories lacking micromanufacturing facilities, such as those related to biology and chemistry, especially in developing countries.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

EXAMPLE 1

Fmold

A photopolymer flexographic master mold (Fmold) was fabricated using a Kodak Flexcel NX and a thermal imaging layer (TIL), which can be a photopolymer film. A microchannel network was designed and transferred to the TIL with an infrared laser source of 2400 pulses per inch (ppi) and, subsequently, it was laminated onto an unexposed photopolymer plate. In the next step, the photopolymer plate was exposed to UVA light at 0.45 J on the reverse side, then the front side was exposed to UVA light at 19 J, and the TIL was removed. Then, the photopolymer plate was washed with solvent PROSOL N-1 at 360 mm/min and dried in an oven for 30 min at 50° C. Then, the photopolymer plate was exposed to UVC light at 10 J for 17 min and UVA light at 4 J for 2 min on the front side. Before use, the Fmold was placed in an oven at 100° C. for 12 hours and then treated in a vacuum chamber for 1 hour at 25° C., followed by being cleaned in 70% ethanol solution in an ultrasonic bath for 7 minutes, dried at 40° C. for 10 minutes, and cleaned in a nitrogen stream.

EXAMPLE 2

ERmold

An epoxy resin mold (ERmold) was fabricated by mixing a commercially available epoxy resin and curing agent by hand-stirring for 3 minutes in a 2:1 weight ratio and ultrasonically treating using a bath-type sonicator (TESTLAB Ultrasonic Cleaner) for 7 min to remove air bubbles. Then, the mixture was poured onto the Fmold and cured at room temperature for 72 hours. After curing, the epoxy resin mold was peeled off from the Fmold to form the male mold, referred to as ERmold.

EXAMPLE 3

Transfer of the ERmold Features to Polymer

PDMS was mixed with a curing agent at a ratio of 10:1. The mixture was placed under vacuum to remove air bubbles. After this, the mixture was poured into the ERmold and cured in an oven at 40° C. overnight. Then, the device was peeled off the mold and cut, and the fluidic connections were punched with a hollow punch with an inner diameter of 1 mm (Integra Miltex®, Ted Pella, Inc). The device was then irreversibly bonded to a glass substrate after exposure to a high-frequency generator (BD 10AS, Chicago, USA) for 15 min. Stainless steel catheters and hoses (0.8 mm diameter) with syringes were connected at the inlet and outlet channels.

EXAMPLE 4

PDMS microfluidic chips were fabricated using a printing plate photopolymer called Flexcel as a master mold (Fmold). The method demonstrated the ability to generate multiple devices from a single master, reaching a minimum channel size of 25 µm, structure height ranging from 53 to 1,500 µm, and dimensions of 1270×2062 square millimeters ($mm^2$), which is larger than those obtained by related art methods. Scanning electron microscopy (SEM), atomic force microscopy (AFM), and profilometry techniques were employed to characterize the Fmold and PDMS replicas. The results showed high replication fidelity of Fmold to the PDMS replica, as well as the reusability of the Fmold. Fifty PDMS replicas have been fabricated using the same Fmold without apparent degradation of the mold. The feasibility of the resulting PDMS replica was effectively demonstrated using a microfluidic device for enhanced oil recovery (EOR) analysis.

Fmold Fabrication

The printing plate photopolymer Flexcel SRH and DITR film used in the fabrication of the Fmolds were supplied by Eastman Kodak. Sheets of 1270×2062 $mm^2$ Flexcel SRH and DITR film were chosen for the fabrication of molds. The photopolymer thickness was around 1.14 mm. The flexographic plate included an elastomeric, styrene-diene-styrene-based photo polymeric sheet on a polyethylene terephthalate base was solvent washable or water washable. The organic compounds were crosslinked by the exposure to UVA wavelengths as crosslinker initiators and UVC wavelengths were used to end the reaction, giving large and stable molecular structures insoluble in the defined developing solution.

Figure 11:
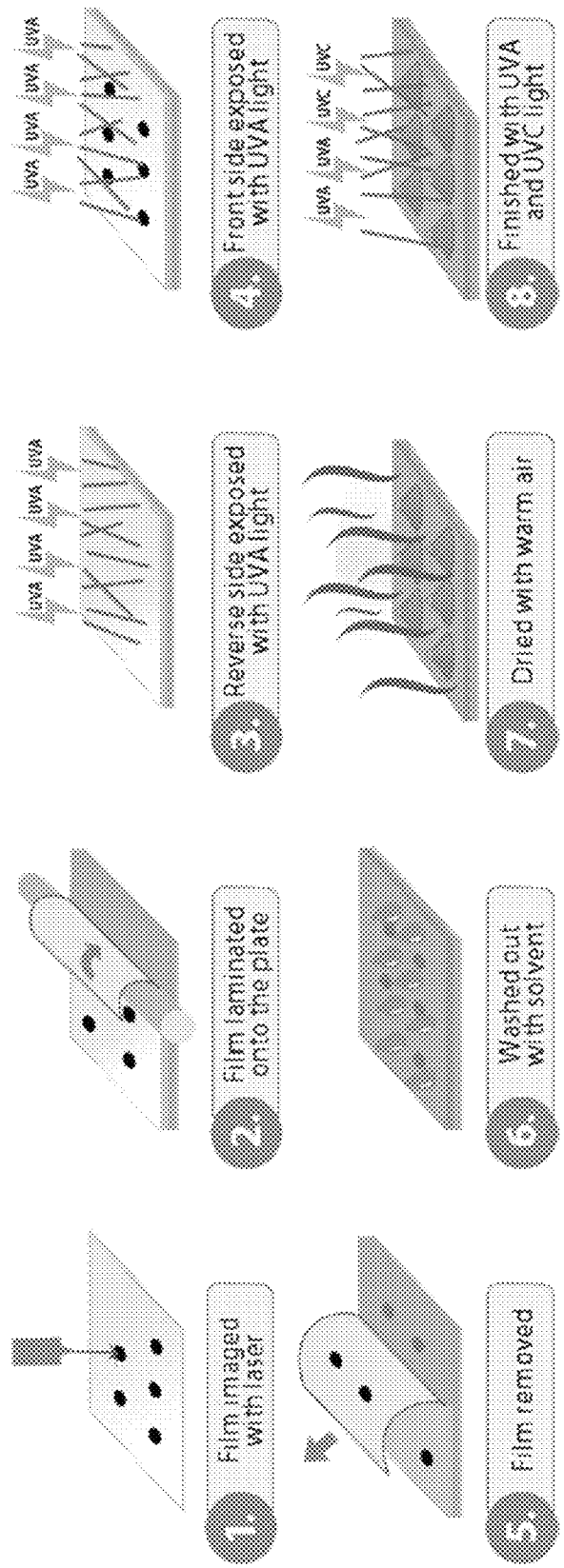
FIG. 11 is a process flow showing fabrication of a master mold (Fmold), according to an embodiment of the subject invention.

FIG. 11 shows a process flow of the fabrication of the master mold (Fmold). Referring to FIG. 11, the microchannel network was designed with Layout Editor software, and the design was transferred to the DITR film with an infrared laser source of 2,400 ppi. Then, the film was laminated onto the unexposed flexographic printing plate before being exposed to UVA light at 0.45 J on the reverse side and UVA light at 19 J on the front for 360 seconds(s). The time of UVA exposure on either side or both sides (e.g., on the reverse side) can vary depending on the desired result. After the exposure, the film was removed, and the flexographic printing plate was washed with solvent PROSOL N-1 at 360 mm/min and dried in an oven for 30 min at 50° C. Next, the flexographic printing plate was exposed to UVC light at 10 J for 17 min and UVA light at 4 J for 2 min on the front. The same procedure was applied to prepare the Fmold used to fabricate the PDMS-floor replica, without layout design application.

The Fmold obtained was then covered with an ultrathin $SiO_2$ film by plasma-enhanced chemical vapor deposition (PEVCD). A PECVD homemade reactor provided an electric continuous power source of glow discharge of 900 V with capacitive coupling and impedance matching. The vacuum chamber was made with a Pyrex glass tube of 80 cm in length and 15 cm in diameter. Hexamethyldisilazane (HMDS) (Dow Corning) was used as a precursor monomer. The working gas ($O_2$) entry was located at the end of the vacuum chamber, far from the substrate, allowing vapor ionization in the area of discharge generation and $SiO_2$ coating production. The coating process was performed according to the conditions described by Lasorsa et al. (C. Lasorsa, P. J. Morando, A. Rodrigo, Surf. Coat. Technol. 2005, 194, 42; which is hereby incorporated herein by reference in its entirety). The PEVCD working conditions were 8 ml/s $O_2$ flow rate, 1 millibar (mbar) gas pressure and 3 h exposure time. The mold without any treatment can be referred to as Fmold, and the mold covered with an ultrathin $SiO_2$ film can be referred to as Fmold-T ($SiO_2$ treated).

PDMS Microdevice Fabrication

PDMS microdevices (Sylgard 184, Dow Corning, USA) were fabricated as previously described by Peñaherrera et al. (A. Peñaherrera, C. Payés, M. Sierra-Rodero, M. Vega, G. Rosero, B. Lerner, G. Helguera, M. S. Pérez, Microelectron. Eng. 2016, 158, 126; which is hereby incorporated herein by reference in its entirety). Briefly, PDMS was mixed with curing agent in a 10:1 ratio. Then, the mixture was placed under vacuum to remove air bubbles, poured onto the Fmold-T and cured in an oven at 40° C. overnight. Before fabrication of each PDMS device, the Fmold-T was silanized using trichloro(1H,1H,2H,2H-perfluor-ooctyl)silane (Sigma-Aldrich, Argentina) via vapor deposition under vacuum.

After curing, the PDMS replica was peeled off from the mold and holes were punched in order to connect it externally to a syringe pump (ADOX—AcTIVA A22). To assemble the microfluidic device, the PDMS replica was irreversibly bonded to a PDMS-floor replica by exposure to oxygen plasma carried out in the PECVD reactor. The PDMS surfaces were first activated by $O_2$ plasma (900 V, 1 mbar, 30 s) to create the —SiOH group on the PDMS surface. After the surface activation, the PDMS replicas were placed in contact immediately.

Characterization

The surface morphology of the Fmolds and PDMS replicas was determined using a field emission gun SEM (TESCAN FEG SEM MIRA3). In order to avoid samples damage, SEM measurements were carried out at voltages between 3 and 5 kV. Previously, the molds were metalized with an approximately 20 nm thick gold layer. Fmold roughness was determined via AFM (Dimension Icon with ScanAsyst, Bruker, Ecuador). AFM images were acquired in ScanAsyst mode at ambient conditions by using a cantilever with a spring constant of 0.71 N/m. The average roughness (Ra) parameter was determined by applying the Nanoscope Analysis 1.8 software to multiple images taken at random positions in scan areas of 50×50 µm². AFM images obtained were reproducible over at least five points on the sample surface. Profilometry measurements were performed using a Dektak XT profilometer from Bruker, and the analysis was carried out using Vision 64 software. The images of the Fmolds and PDMS microdevices were taken with a binocular magnifier (Biotraza) attached to a digital camera.

Applications

Figure 10:
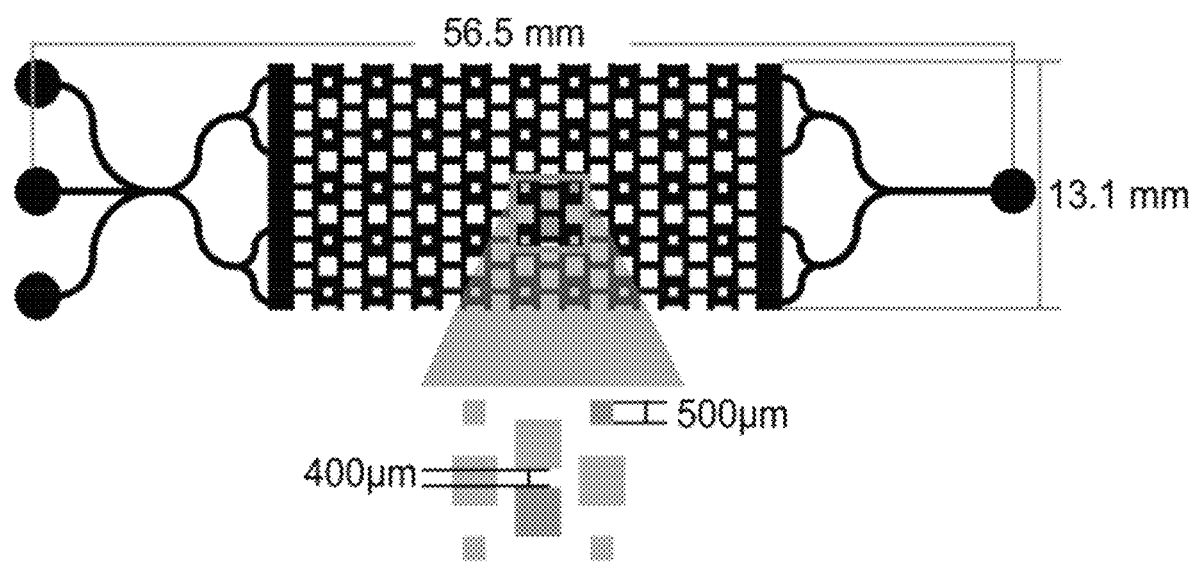
FIG. 10 is a top view of a microfluidic device according to an embodiment of the subject invention, used for an enhanced oil recovery (EOR) experiment. The dimensions shown are for exemplary purposes only and should not be construed as limiting.

In order to demonstrate the usefulness of the Fmold methodology for PDMS microdevices fabrication, microfluidic chips were designed and employed for EOR applications. FIG. 10 shows the design of the microfluidic device used for EOR experiments. Porosity, poral volume (PV), and height were to 32%, 22 µL, and 81 µm, respectively. The pore throat sizes were 400 µm and 650 µm.

The oil recovery experiment was performed using crude oil, deionized water with acid blue dye, and polyacrylamide polymer (1000 ppm). The crude oil used had a density of 0.81 grams per milliliter (g/ml) and a viscosity of 4.42 centipoise (cP) at 25° C. Before injection of oil into the microfluidic device, its impurities were removed by rotating the oil in a centrifuge. A binocular magnifier was used to observe the flow inside the channel, and a Canon T3-I Rebel digital camera attached to the loupe recorded the phenomena. Images were obtained and the analysis was performed using Fiji by Image J software. The methods described herein provide accessible and cost-effective alternatives to fabricating PDMS microdevices compared to related art methods. Data obtained through mold characterization provided information for the application in the microfluidic field of EOR assays.

Mold Characterization

Figure 12:
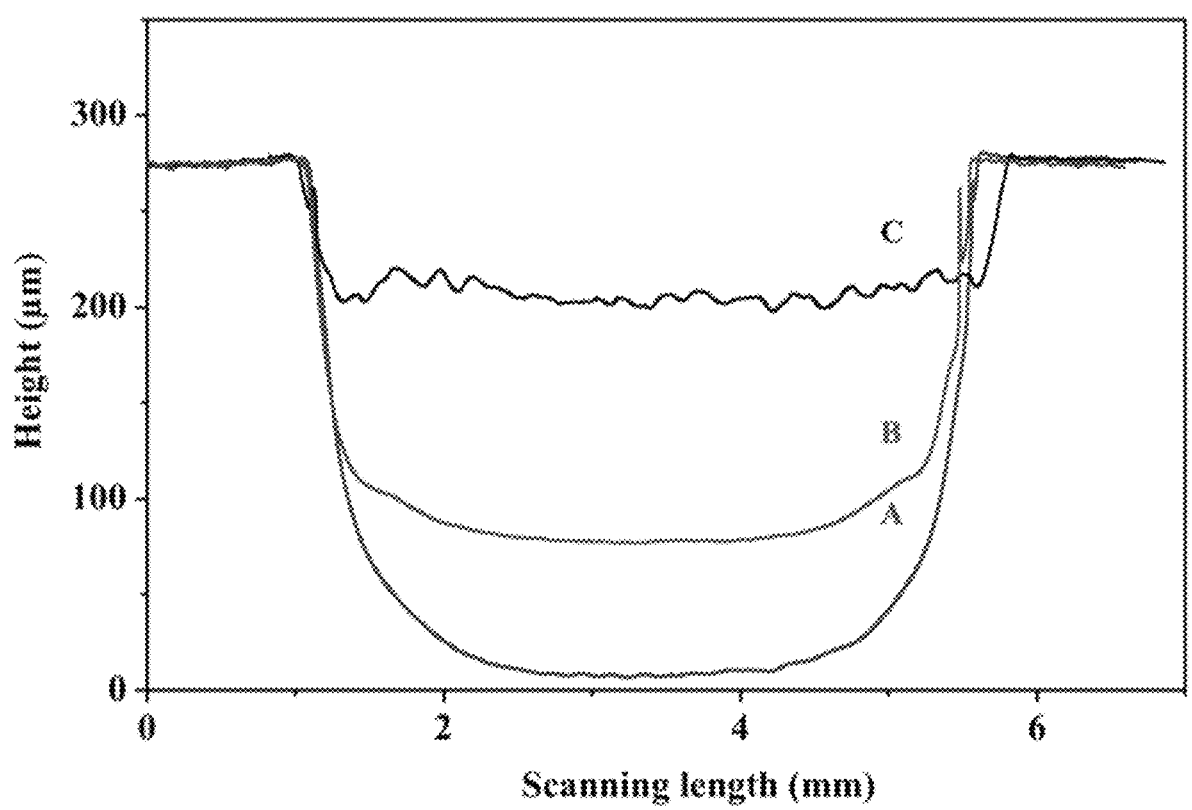
FIG. 12 is a plot showing height (in micrometers (μm)) versus scanning length (in millimeters (mm)) for structures formed in Fmold. These are shown for ultraviolet-A (UVA) exposure time on the reverse side of: 35 seconds (labeled "A" in the plot), 40 seconds (labeled "B"), and 48 seconds (labeled "C"). "A" is the lowermost line at 4 mm; "B" is the middle line at 4 mm; and "C" is the uppermost line at 4 mm. The height measurements were determined by a profilometry technique (n=3).
Figure 13:
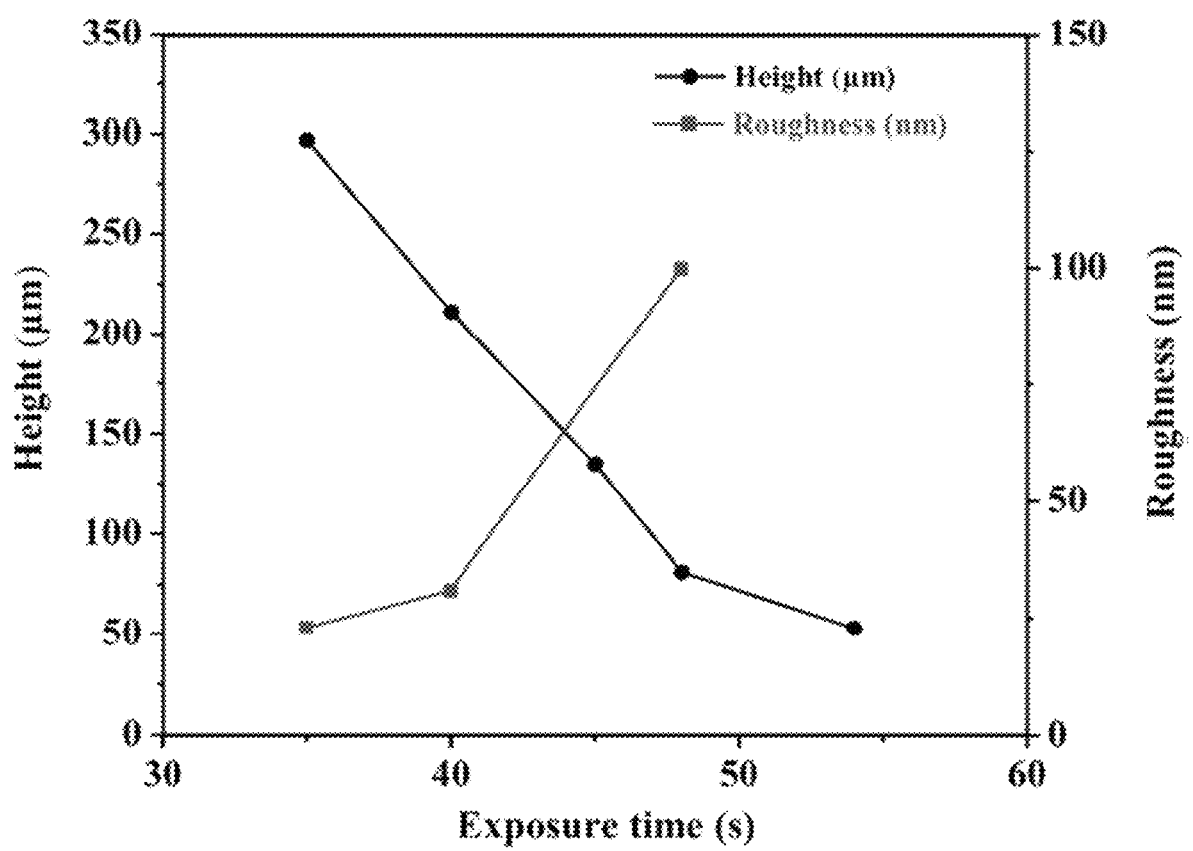
FIG. 13 is a plot of height (in μm) (left vertical axis) versus exposure time (in seconds (s)) and roughness (in nanometers (nm)) (right vertical axis) versus exposure time showing the effect of reverse side UVA exposure times on the height of structures and on surface roughness. The lowermost line at 35 s is for surface roughness; and the uppermost line at 35 s is for height.
Figure 14A:
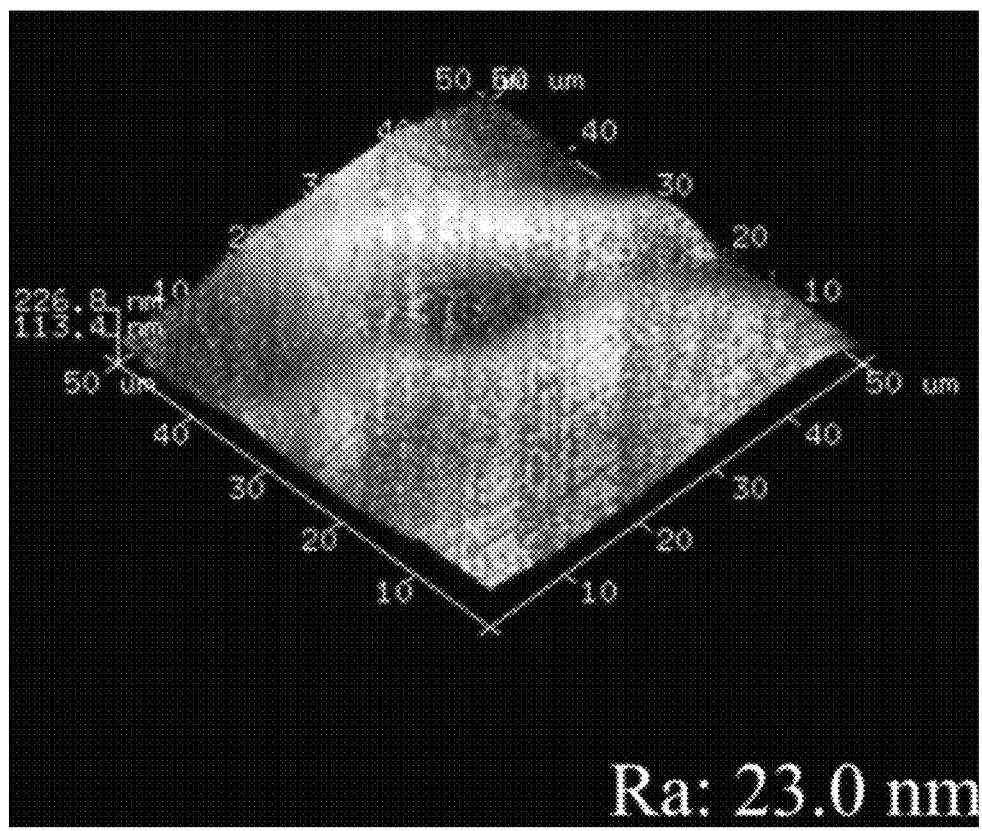
FIGS. 14A-14C are atomic force microscopy (AFM) image of a mold surface. Ra represents the average roughness value.
Figure 14B:
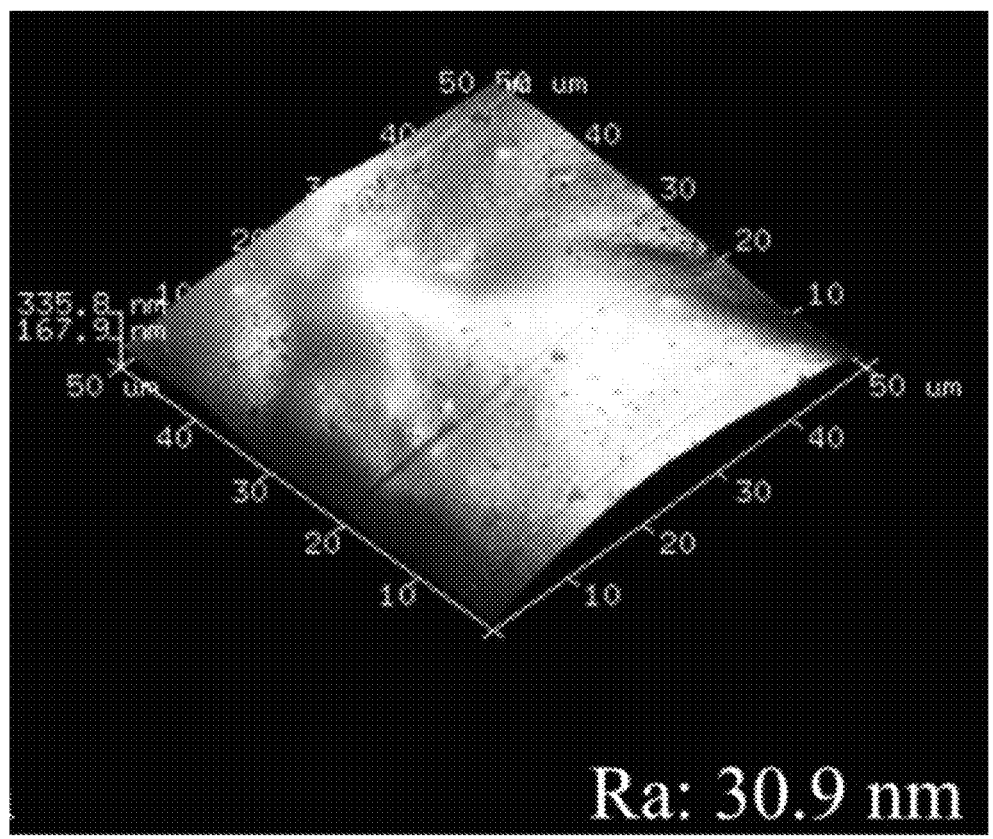
Figure 14C:
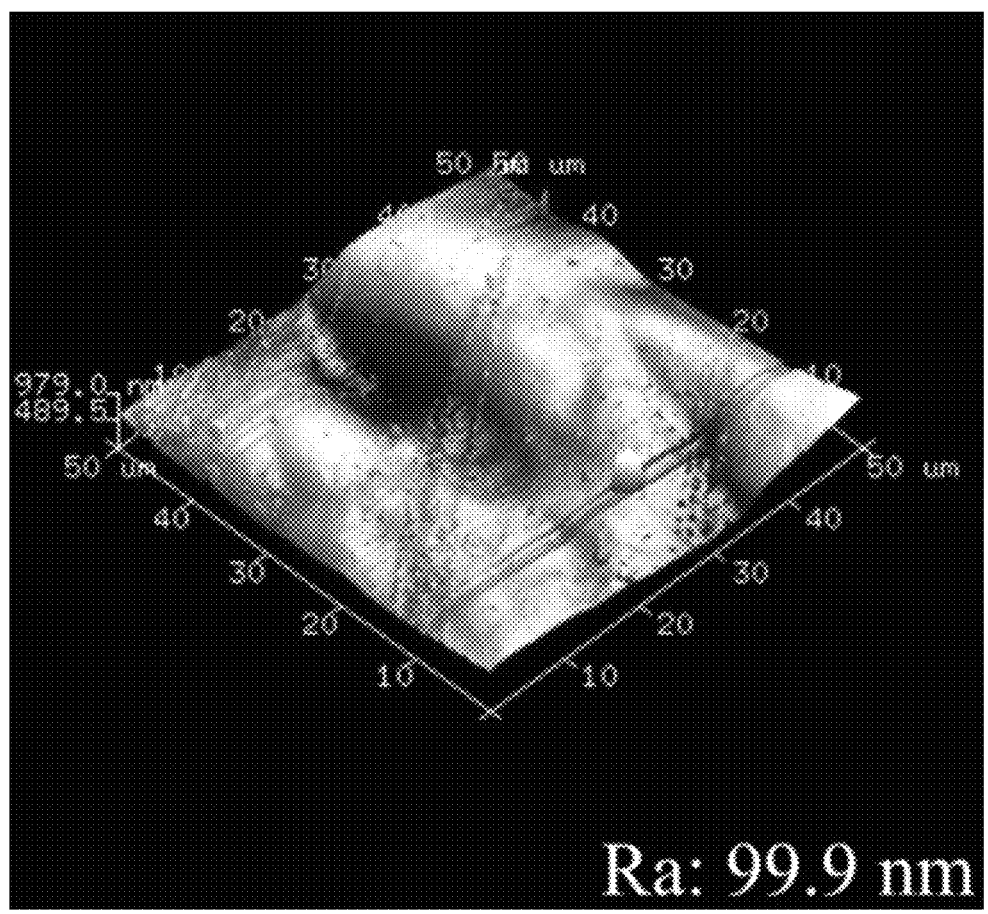

FIG. 12 is a plot showing height (in micrometers (µm)) versus scanning length (in millimeters (mm)) for structures formed in Fmold. These are shown for ultraviolet-A (UVA) exposure time on the reverse side of: 35 seconds (labeled "A" in the plot), 40 seconds (labeled "B"), and 48 seconds (labeled "C"). "A" is the lowermost line at 4 mm; "B" is the middle line at 4 mm; and "C" is the uppermost line at 4 mm. The height measurements were determined by a profilometry technique (n=3). FIG. 13 is a plot of height (in µm) (left vertical axis) versus exposure time (in seconds (s)) and roughness (in nanometers (nm)) (right vertical axis) versus exposure time showing the effect of reverse side UVA exposure times on the height of structures and on surface roughness. The lowermost line at 35 s is for surface roughness; and the uppermost line at 35 s is for height. Based on the results shown in FIGS. 12 and 13, an inverse relationship between UVA exposure time and structure height was demonstrated. Also, the effect of the UVA exposure time on the surface morphology was studied by measuring the roughness of Fmolds. AFM images and the corresponding average rough-ness (Ra) values are presented in FIGS. 14A-14C. In FIGS. 14A-14C, Ra represents the average roughness value. FIG. 14A is for a UVA exposure time of 35 s on the reverse side; FIG. 14B is for a UVA exposure time of 40 s on the reverse side; and FIG. 14C is for a UVA exposure time of 48 s on the reverse side. The AFM images and roughness values show that the surface changes with different UVA exposure time.

The order of Ra parameter values were: A—23 nm (35 s)<B: 30.9 nm (40 s)<C: 99.9 nm (48 s). The Fmold C is much rougher than the Fmold B and A. Specifically, changes on the Fmold surface roughness can be attributed to changes on the crosslinking degree in the material, as well as modifications in the type of bonds in the surface layer caused by the UVA treatment. In comparison with related art molds, Fmold presents higher roughness than the SU-8 resin (~10 nm) but lower than the mold roughness manufactured by 3D Systems (~2 μm), micromilling (~0.5 μm), and laser ablation (~7 μm).

A direct dependency between UVA exposure and roughness of the surface was found, and a prolonged UVA radiation causes a decrease in height (FIG. 13). These results provide valuable information on surface properties, which is relevant in the application of the microfluidic devices. Fmolds with dimensions of a standard test target (USAF 1951) were fabricated by applying UVA exposure time on reverse side at times of 54 s and 45 s, obtaining height measurements of 53 μm and 135 μm, respectively. These measurements are included in FIG. 13.

Figure 15:
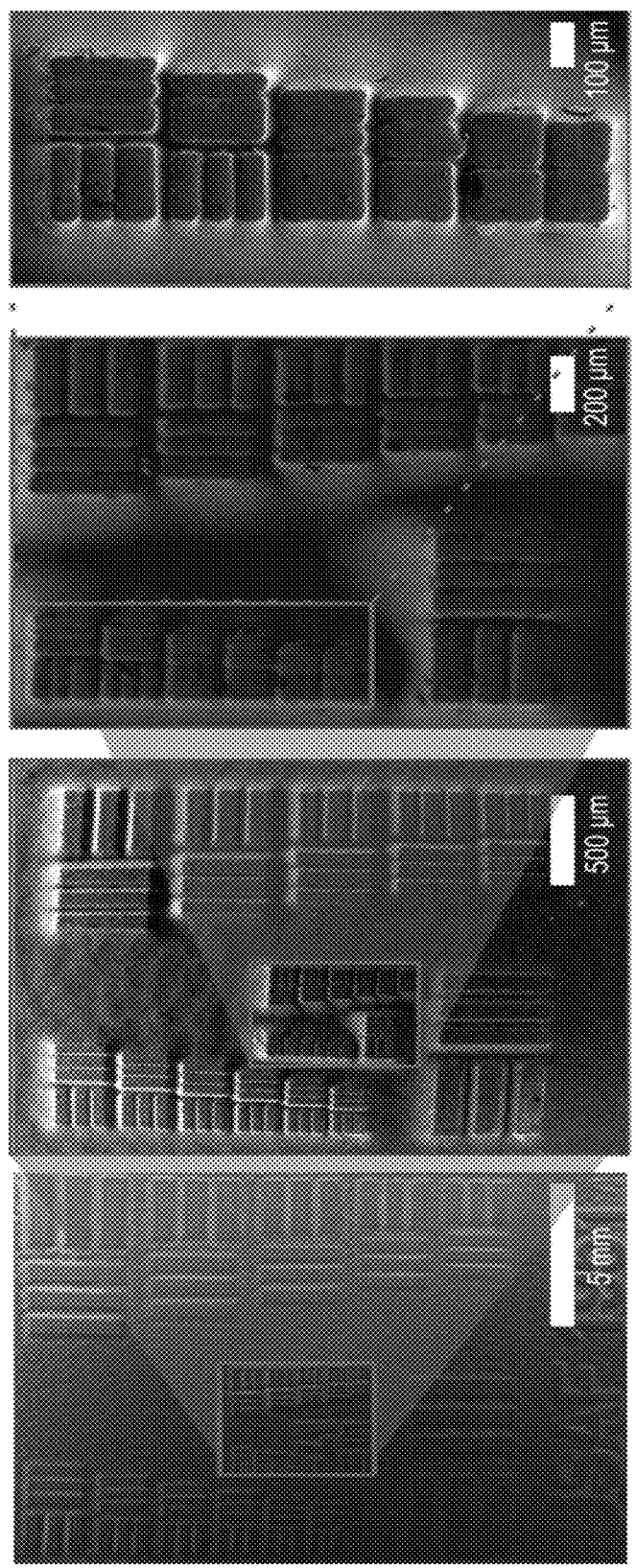
FIG. 15 shows scanning electron microscopy (SEM) images of structures embossed from Fmold, with fabrication conditions as follows: first step UVA exposure time of 54 s on reverse side=54 s; and UVA front side exposure of 360 s.

FIG. 15 shows SEM images of Fmold with rectangular structures and dimensions acquired from the standard test target (USAF 1951). The width of the structures was designed with Layout Editor software and was in a range of from 10 μm to 520 μm. The images indicate uniformly distributed rectangular forms, with structures ranging from 25 μm to 520 μm. SEM images of Fmold evidences the inclination of the structure sidewalls. Widths less than 25 μm were not resolved. The relationship of the sidewall inclination with UV exposure shows proportionality between face exposure and the shoulder angle.

Figure 16:
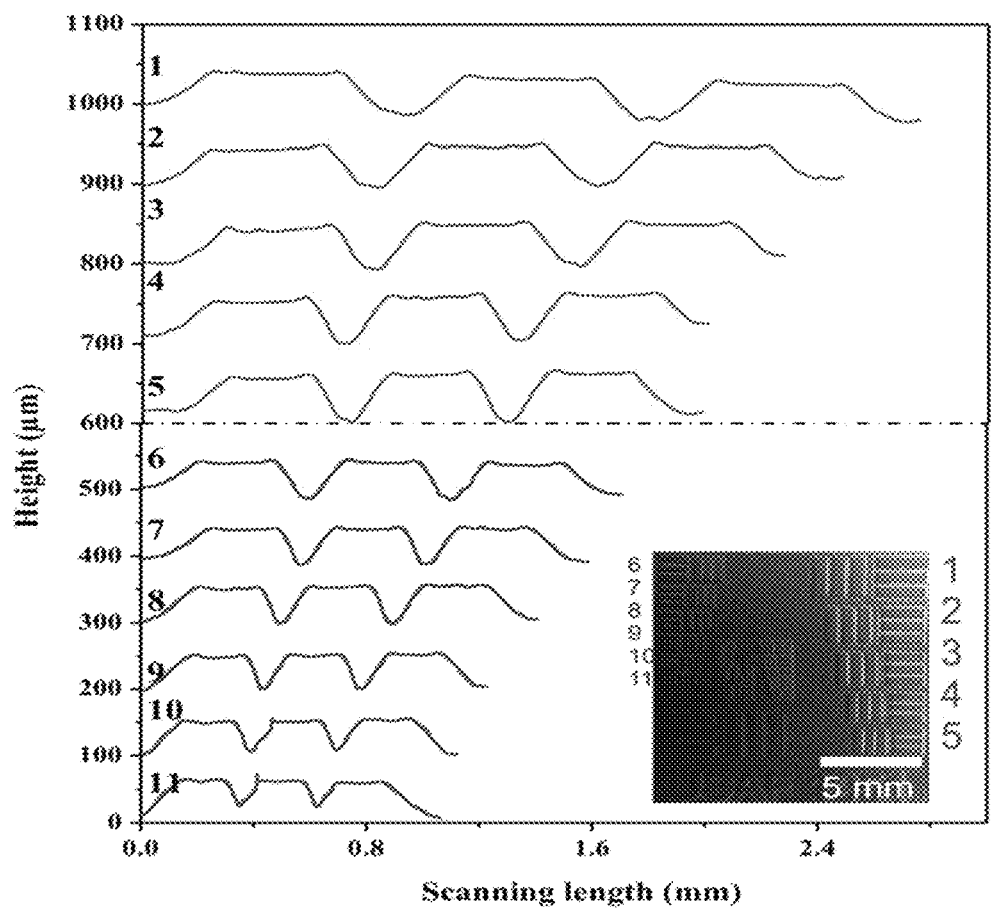
FIG. 16 shows a plot of height (in μm) versus scanning length (in mm) of Fmold recorded by profilometry. The inset shows an SEM image of the mold. The Fabrication conditions were as follows: first step UVA exposure time of 54 s on reverse side; and UVA front-side exposure of 360 s. Height measurements were determined by a profilometry technique (n=3).

Structure height uniformity was tested by profilometry. FIG. 16 shows that the height of the structures labeled in the figure as numbers 1-9 exhibit an average of 53 μm, whereas the structures labeled as 10 and 11 show values of 42 μm and 38 μm, respectively. The differences of heights are due to the inclination of the structures, causing an overlapping.

Figure 17A:
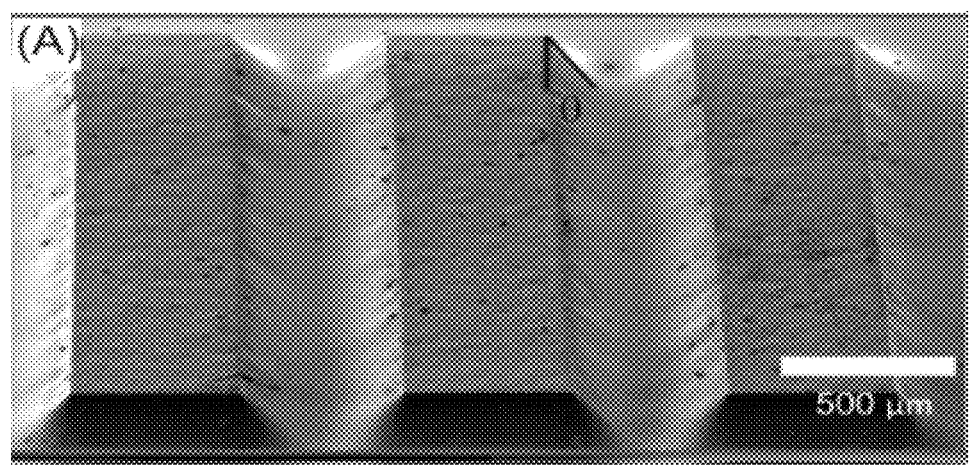
FIG. 17A shows an SEM image of a perspective view of an Fmold according to an embodiment of the subject invention.
Figure 17B:
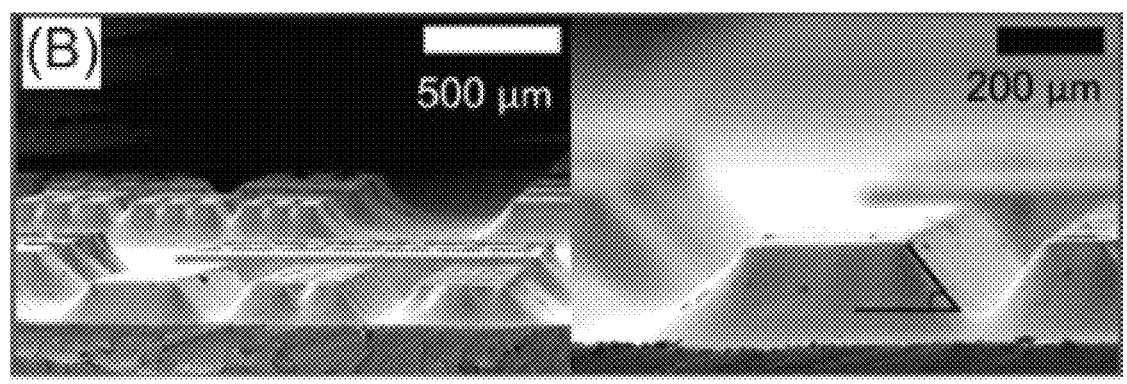
FIG. 17B shows an SEM image of a cross-sectional view of an Fmold according to an embodiment of the subject invention.
Figure 17C:
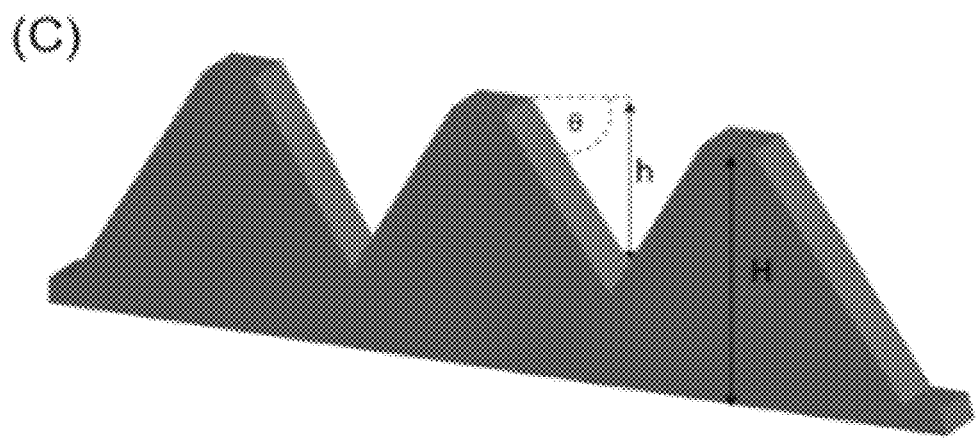
FIG. 17C shows a schematic representation of the resulting structure height from overlapping.
Figure 17D:
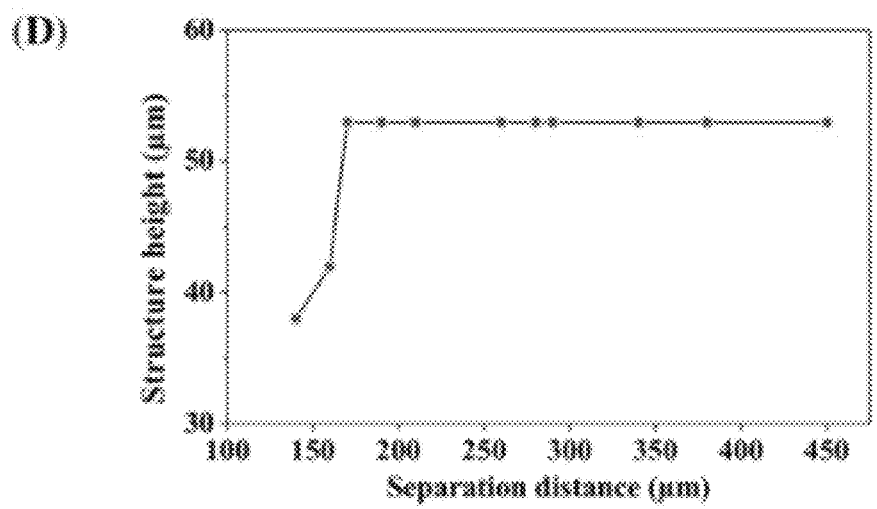
FIG. 17D shows a plot of structure height (in μm) versus separation distance (in μm), showing how the structure height varies as the separation distance varies.

FIGS. 17A and 17B show SEM images of the cross-section of the Fmold, showing trapezoidal shapes of the structures. This characteristic shape generates an overlapping of continuous structures as shown in the schematic representation in FIG. 17C. FIG. 17D shows the comparison of structure height at different separation distances. The height is uniform while the separation distance between structures is higher than 170 μm, demonstrating that the trapezoidal shape is not a limitation for PDMS device fabrication. Related art SU-8 structures have had this shape when a microfluidic neuron culture device is fabricated (M. Kang, J. H. Byun, S. Na, N. L. Jeon, RSC Adv. 2017, 7, 13353).

The results demonstrate that Fmolds with different channel dimensions (length, width, and height) can be obtained (e.g., desired length, width, and/or height for a particular use or application). Structures with a minimum width of 25 μm and heights up to 1500 μm can be made, achieving an aspect ratio (height/width) of 60. Regarding the length, it is possible to make multiple molds with a wide variety of dimensions. In addition, they can be manufactured with a total size as desired (e.g., 1270×2062 mm$^2$, or a larger size if desired).

PDMS Microdevices Fabrication

Figure 18A:
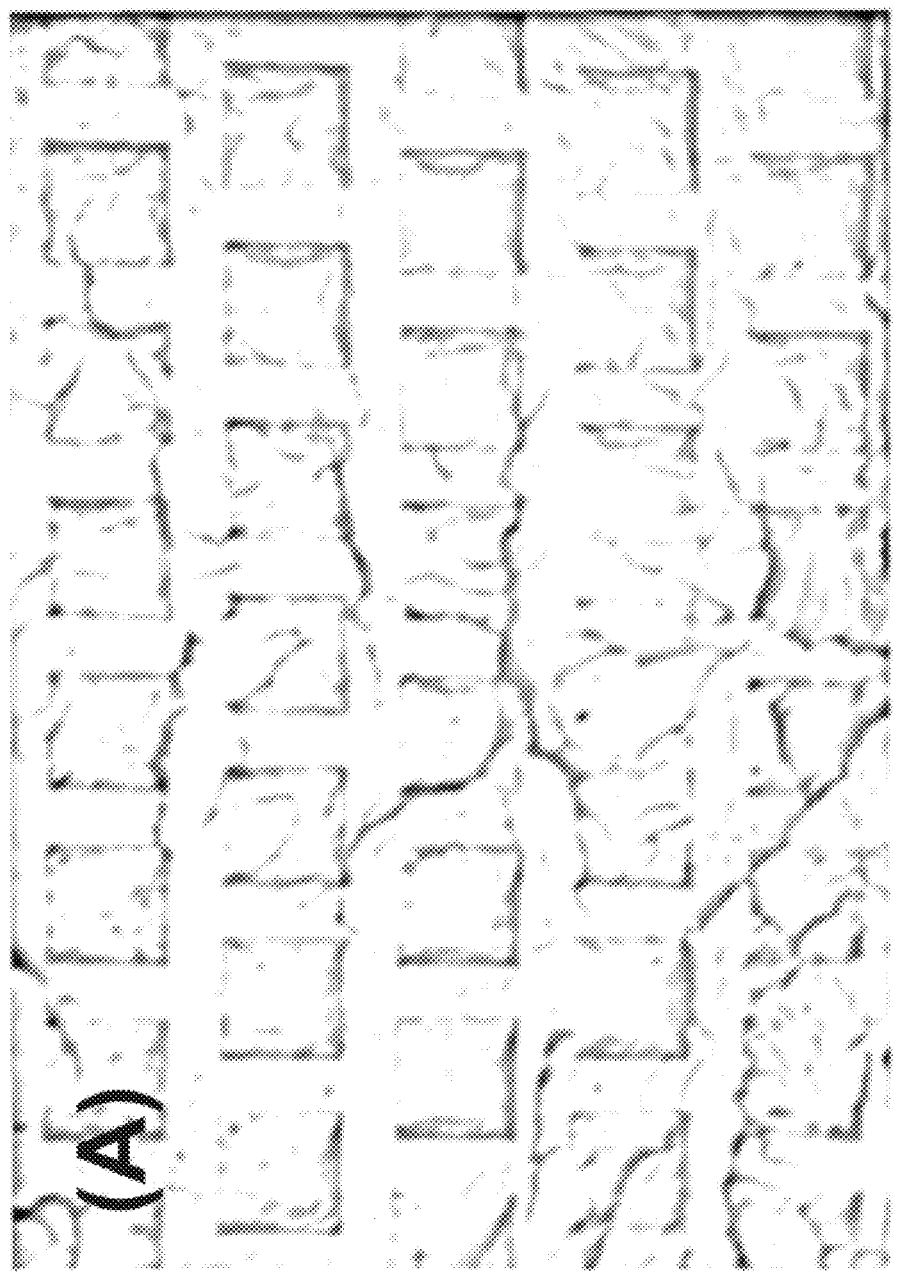
FIG. 18A shows an image of a fresh Fmold according to an embodiment of the subject invention, obtained after polydimethylsiloxane (PDMS) replica manufacturing.
Figure 18B:
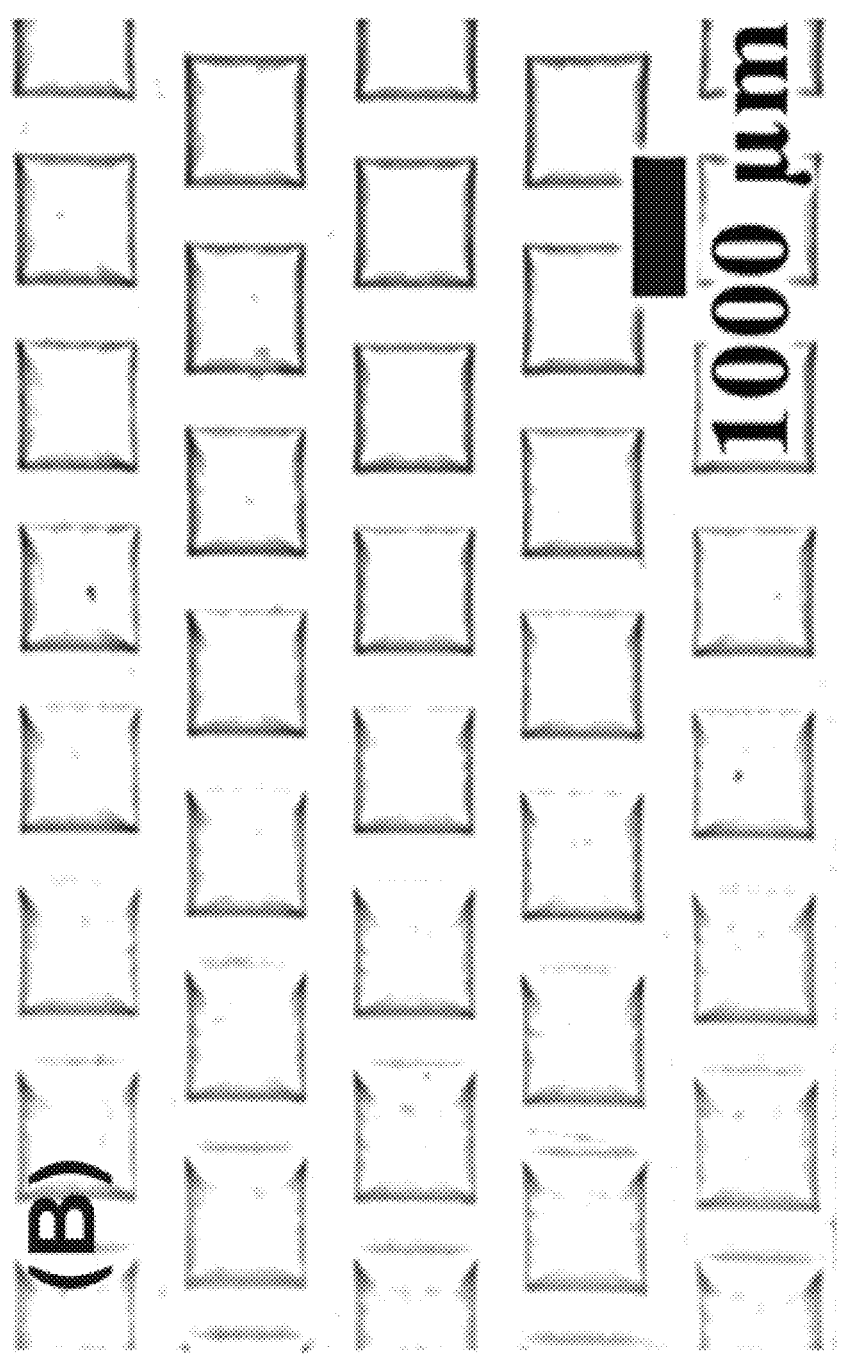
FIG. 18B shows an image of an Fmold according to an embodiment of the subject invention, obtained after polydimethylsiloxane (PDMS) replica manufacturing, and coated with silicon dioxide ($SiO_2$). This can be referred to as "Fmold-T".

The Fmold fresh template and Fmold treated with SiO$_2$ (Fmold-T) were evaluated to optimize PDMS microdevice fabrication. The Fmold was fabricated using a design that has homogeneous squares with dimensions of 1000 μm and separation between structures of 400 μm. Several replicates can be obtained using the same Fmold; however, PDMS residues may adhere to the mold as a result of the affinity between the Flexcel polymer and PDMS (see FIG. 18A). To solve this problem, an SiO$_2$ coating was used. Consequently, using Fmold-T, an adequate demolding was obtained and no residues of adhered PDMS were observed (see FIG. 18B). This is because the SiO$_2$ thin film deposited on the Fmold-T avoids undesirable stickiness between the PDMS and the mold. As an alternative to the PDMS microdevices fabrication process using the Fmold-T technique, epoxy resin replicas from the Fmold were tested.

Silanization treatment with trichloro (1H,1H,2H,2H-perfluorooctyl)silane on a silicon surface is a common method to facilitate the demolding process of PDMS microdevices as well as to protect the integrity of the master mold. The coupling of perfluorinated organosilane molecules to the silicon surface decreases its surface energy and promotes the release from the PDMS. Therefore, a silanization treatment of the Fmold-T was performed. Two treatments of silanization-exposure times under vacuum were tested, at 1 h and at 3 h. Because no differences were found with both treatments, the Fmold-T was silanized using the shortest time.

Figure 19A:
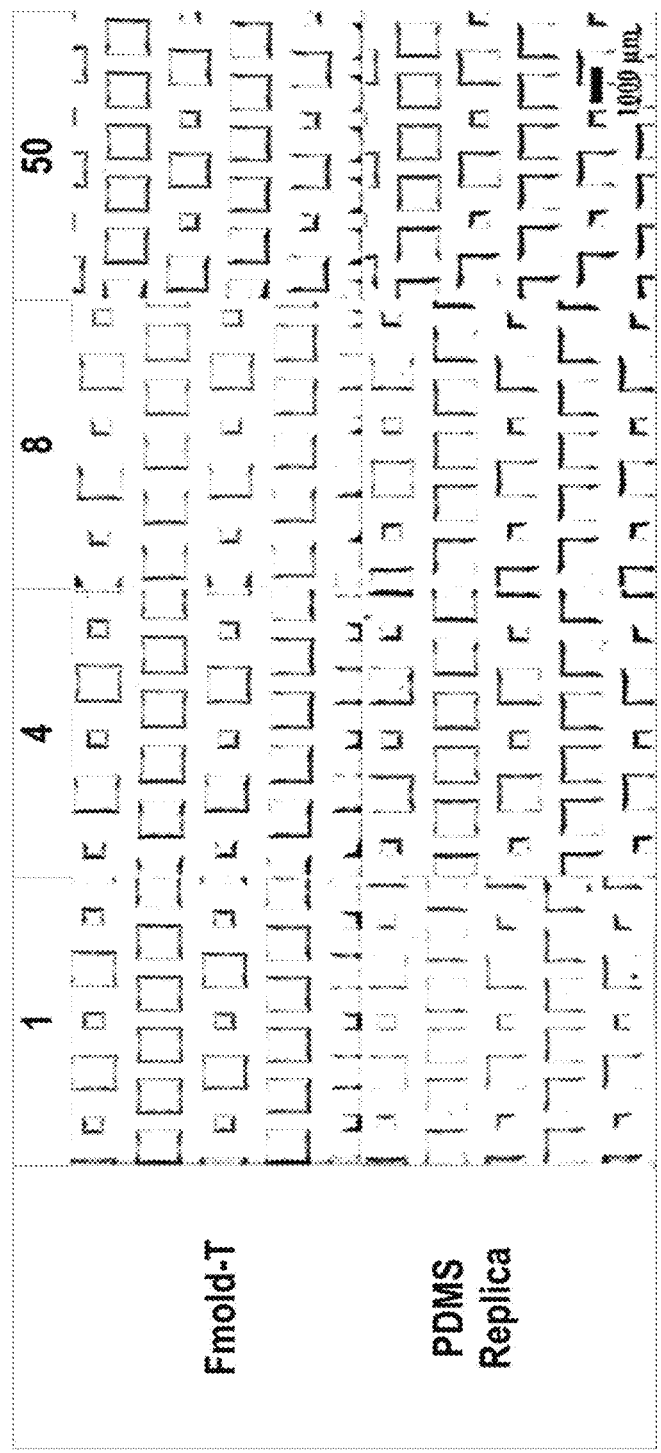
FIG. 19A shows magnified images of Fmold-T (top row) and PDMS replica (bottom row) molds at the first (first column), fourth (second column), eight (third column), and fiftieth (fourth column) PDMS replicas. Fabrication conditions included first step UVA exposure time of 42 s on reverse side=42 s. The scale bar is 1000 μm.
Figure 19B:
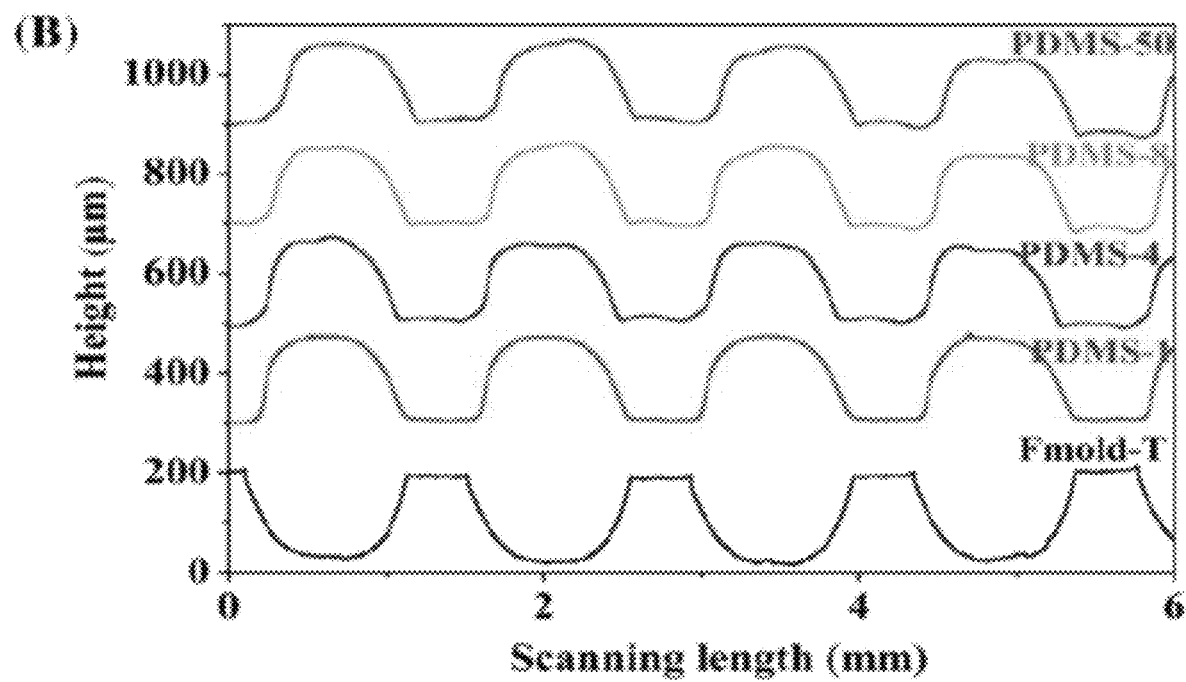
FIG. 19B is a plot of height (in μm) versus scanning length (in mm) for Fmold-T (bottom line) and PDMS replicas at the first ("PDMS-1"), fourth ("PDMS-4"), eight ("PDMS-8"), and fiftieth ("PDMS-50") PDMS replicas. Fabrication conditions included first step UVA exposure time of 42 s on reverse side=42 s. Height measurements were determined by a profilometry technique (n=3).

To demonstrate the replication fidelity of the method, 50 PDMS replicas were fabricated using the same Fmold-T. FIG. 19A shows the binocular magnifier images of Fmold at the 1st, 4th, 8th, and 50th PDMS replicas. For the replicas, a design with heterogeneous squares was used. FIG. 19B shows the height measurements recorded by profilometry from the Fmold-T and PDMS replicas. The comparison between the structure dimensions of the Fmold-T and the PDMS replicas indicates that the height and depth vary less than 10%, which demonstrates that PDMS can be replicated with high fidelity, with these values being comparable to typical in-plane photolithographic tolerances of approximately 10%. High fidelity of replication was also observed in the analysis of Fmold-T and PDMS replica of a standard test target (USAF 1951) by SEM and profilometry. Comparison of width, height, and depth of channels showed a low variation (<10%) on the entire range of the channels. The Fmold-T can be used many times to get PDMS replicas without apparent degradation in featured mold dimensions, demonstrating the reusability and durability of the Fmold-T and therefore decreasing manufacturing costs.

It is known that molds made in silicon wafers with photoresin have a limited lifetime because structures created with this material are prone to be released from the wafer. In the case of the Fmold-T, the mold with the structure of interest forms a single monolithic element, so there is no possibility of detachment of the structures. Also, the inclination of the sidewalls can reduce post-detachment contact and frictional resistance between the replicated structure (PDMS) and Fmold-T, allowing a better demolding. This is an advantage especially when the structures formed in the mold have a high aspect ratio. In the case of SU-8 resin, mold angles are smaller than 90° and present difficulties in the demolding process. This is why the SU-8 resin tends to be delaminated from the support (generally silicon wafers), especially when the structures have a high aspect ratio.

Devices fabrication through printing plate photopolymers have been described previously (A. W. Browne, M. J. Rust, W. Jung, S. H. Lee, C. H. Ahn, Lab Chip 2009, 9, 2941; J. Olkkonen, K. Lehtinen, T. Erho, Anal. Chem. 2010, 82, 10246; S. Kim, H. Sojoudi, H. Zhao, D. Mariappan, G. H. McKinley, K. K. Gleason, A. J. Hart, Sci. Adv. 2016, 2, 1). However, none have the ability to fabricate a photopolymer master mold of large size (e.g., centimeter scale or greater, reaching 1270×2062 mm$^2$ or larger) at low cost.

EXAMPLE 5

PDMS Device Applied to Fluid Injection and EOR Analysis

PDMS devices fabricated according to the process set forth in Example 4 were tested. The functionality of the device for EOR was evaluated for injecting, oil, water, and a commercial polyacrylamide polymer. The microdevice was fully injected with crude oil at a flow rate of 1.0 ml/h until it was successfully trapped in the pore space, and the next step was the injection of water at a flow rate of 0.5 ml/h and 2.0 ml/h to reach residual oil saturation. Then, polyacrylamide polymer solution (1000 ppm) was injected at 0.5 ml/h and 1.0 ml/h. Standard image analysis using Image J was used to determine the percentage of oil recovered. The difference between the initial state of the black pixels and the final state was interpreted as oil recovery.

Figure 20:
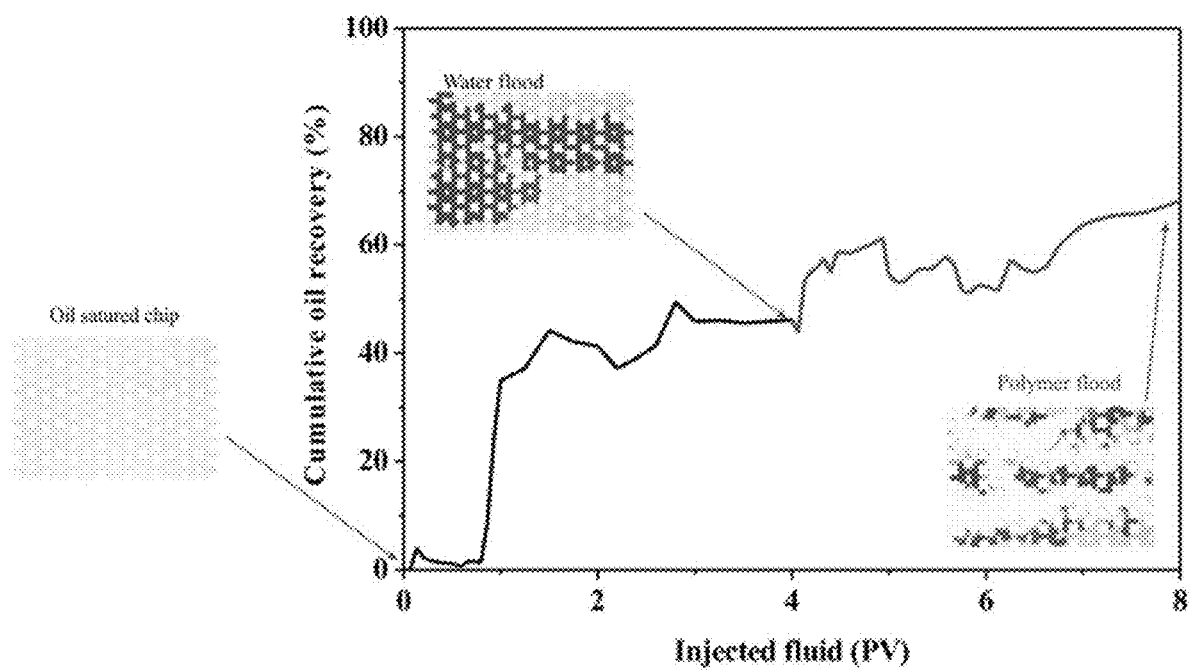
FIG. 20 shows a plot of cumulative oil recovery (in %) versus injected fluid (poral volume (PV)) for an oil recovery analysis. Inset are images of an oil saturated chip, a dyed water flood, and a polymer flood.

FIG. 20 shows a plot of cumulative oil recovery (in %) versus injected fluid (poral volume (PV)) for an oil recovery analysis. Inset are images of an oil saturated chip, a dyed water flood, and a polymer flood. Referring to FIG. 20, the oil recovery in relation with PV and the images obtained in each stage are shown, which depict water and polymer flowing into the pore space and displacing crude oil. It can be seen that water injection at a flow rate of 0.5 ml/h displaces the crude oil from the channels, giving an oil recovery of 37% (1.25 PV); when the flow rate increases to 2.0 ml/h, the oil recovery increases to 46% (4 PV). Polymer flooding recovery was 5% (6.1 PV) at a flow rate of 0.5 ml/h and 21% (8 PV) at a flow rate of 1.0 ml/h, giving a total 21% of oil recovery. The total oil recovery achieved was 67%.

Comparison of Availability, Costs, and Resolution of Different Mold Manufacturing Technologies It is well known that developed countries have a higher index of laboratories and publications in almost all areas of science than developing countries. In microfluidics, this effect is particularly marked because for the fabrication of devices of quality and good resolution, it is necessary to have expensive equipment to manufacture the photomasks and molds. While the SU-8 mold cost is relatively low for research groups with manufacturing facilities (without considering cleanroom maintenance expenses and equipment amortization), the cost of acquiring SU-8 molds is very high for research groups with no manufacturing equipment. Due to their high cost, these facilities are practically nonexistent throughout the southern hemisphere. For example, in Argentina, there are only three cleanrooms, which are not always available for research groups outside the institution. One option to carry out the assays would be to hire the service of chip manufacturers outside the country, but there are few companies or universities in the world offering this service. The price of a SU-8 mold charged by these companies is around $400-$800 USD, depending on the required resolution (quote by Flow-JEM). These prices are too high for research laboratories in developing countries, where grants awarded on average may not exceed $3700 per year. As a result, throughout the southern hemisphere, there are only eight of a total of 344 reported research groups investigating microfluidics. Something similar happens with microfluidics companies, finding only one in the whole southern hemisphere.

The methods of embodiments of the subject invention, including those described in Example 4, provide great advances in the field of microfluidics because they allow all laboratories the ability to work in the area of microfluidics (including those in developing countries) without the need for micro manufacturing facilities or equipment to create a master mold. The Flexcel technology can be commercially obtained at a much lower cost than SU-8 molds, as it is commonly used in the graphics industry and it can be acquired worldwide (including in developing countries). In contrast to the 20 companies or universities offering photolithography services, there are now more than 400 companies distributed in 60 countries offering services that could be used for Fmold manufacturing. Regarding the costs, as an example an Fmold of 220×350 mm$^2$ would cost about $35 in Argentina and about $50 in Spain. These prices are at least 10 times less expensive than SU-8 commercial molds, and more accessible to developing laboratories.

At present, there are other alternative methodologies to SU-8 molds, some of which are shown in Table 1. Nevertheless, these techniques do not achieve the resolution of the photoresin or the processes are expensive and inaccessible, so the traditional technique of photoresin molds is still the most used in microfluidics. Table 1 shows a comparison of the minimum channel width achieved by Fmold and other methods of microfluidic mold fabrication. These values range between 21 and 200 μm, and therefore the minimum channel width obtained in Example 4 is well-suited for microfluidic device manufacturing.

TABLE 1

Minimum Channel Width of Methods of Microfluidic Mold Manufacture

| Mold technique | Channel width (μm) |
| --- | --- |
| Stainless steel stamp | 21 |
| Fmold | 25 |
| Toner | 26.6 |
| Liquid molding | 40 |
| 3D printing | 45 |
| Liquid molding | 60 |
| Building blocks | 100 |
| Laser ablation | 120 |
| Semi-contact writing | 140 |
| Laser swelling | 190 |
| 3D printing | 200 |
| WAX mold | 200 |

3D printing is one of the best-known alternative techniques, but its applicability has been limited in part by the technical inability to print reliable microfluidic channels with dimensions less than several hundreds of microns in a reasonable sized device at a reasonable price. Among the main disadvantages of 3D printing are the removal of the support material from small fluidic features, a relatively wasteful print process, and channels with rough surfaces. As the cost of 3D printing equipment decreases, the channel resolution obtained precipitously decreases as well. For example, a PDMS chip produced by 3D printing at a cost of about $2 has a minimal cross-sectional area of 200 μm. High resolution channels obtained by 3D printing have been reported in some research works, but the cost of the equipment is very high (Envision TEC, about $93,000, resolution of 16 μm), or the equipment is homemade (W. Lee, V. Lee, S. Polio, P. Keegan, J. H. Lee, K. Fischer, J. K. Park, S. S. Yoo, Biotechnol. Bioeng. 2010, 105, 1178). In both cases, the molds produced are not commercially available at a global level.

EXAMPLE 6

Assays were run to demonstrate the validity and effectiveness of a BM bioreactor according to an embodiment of the subject invention for the growth of E. coli bacteria and the production of a recombinant intracellular protein. A BM bioreactor having a cistern design as seen in FIG. 4, with the characteristics displayed in Table 2, was fabricated. FIG. 1 shows an image of the BM bioreactor with a U.S. penny for size reference.

Figure 2:
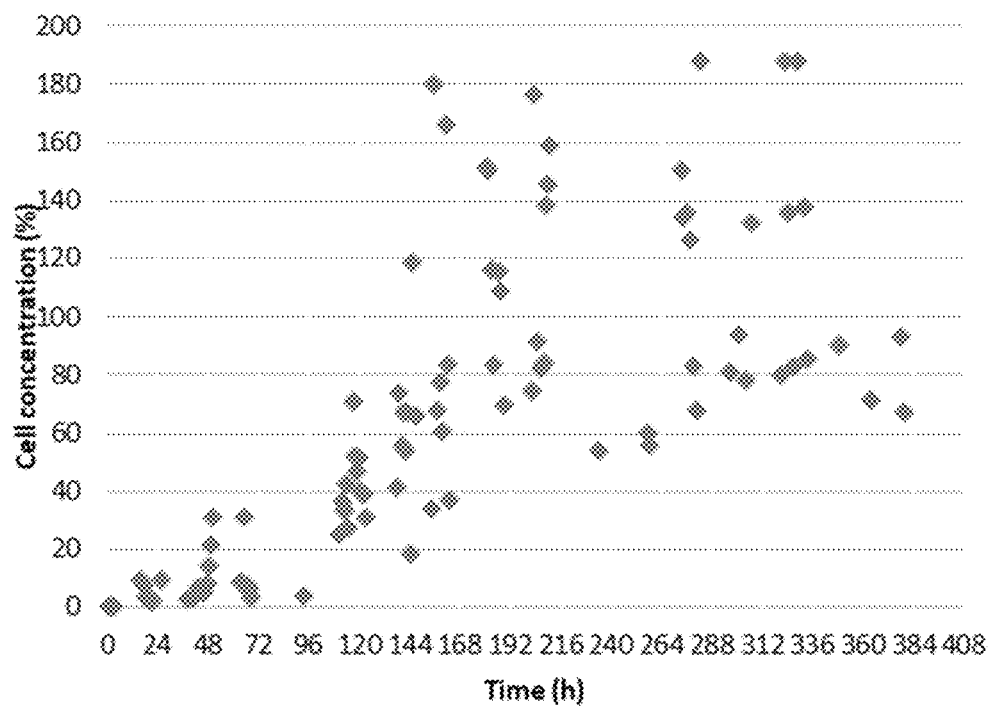
FIG. 2 is a plot of cell concentration (in %) versus time (in hours (h)) for growth of an *E. coli* that produces human recombinant protein in a BM bioreactor according to an embodiment of the subject invention, at a continuous condition.

The BM bioreactor was fed with a 25% dilution of an overnight inoculum of E. coli at a flow rate of 12.8 microliters per minute (μL/min). The dilution was maintained at 25% of fresh overnight inoculum in the inlet of the BM bioreactor, and in the outlet the optical density at 600 nm was measured to calculate the percentage of dilution output vs. time in hours. The results are shown in FIG. 2. The cisterns were filled with microbial biomass as the BM bioreactor was fed with bacteria, and an increase in biomass was observed as a function of time until reaching a concentration of 180% with respect to the initial inoculum at 336 h of continuous culture in the BM bioreactor. After 380 hours of biomass production in the BM bioreactor, a total of 3.84 times more of the input inoculum was reached (see Table 3). The results showed good growth of E. coli in the BM bioreactor.

TABLE 2

Cistern BM bioreactor characteristics

| BM bioreactor-cisterns design | Value | Unit |
|---|---|---|
| Total area | 3830.93698 | mm$^2$ |
| Height | 0.2 | mm |
| Volume | 766 | μL |
| Cisterns number | 16 | |
| Cistern length | 87.83 | mm |
| Cistern width | 2.394 | mm |

TABLE 3

Production of E.coli biomass in the BM bioreactor

| Time (h) | Inoculum 100% input (mL) | Culture medium grown to 100% output (mL) | Ratio input/output |
|---|---|---|---|
| 0-120 | 12341.36 | 5514.55 | 0.66 |
| 121-80 | 24825.21 | 86535.63 | 3.84 |

Figure 3:
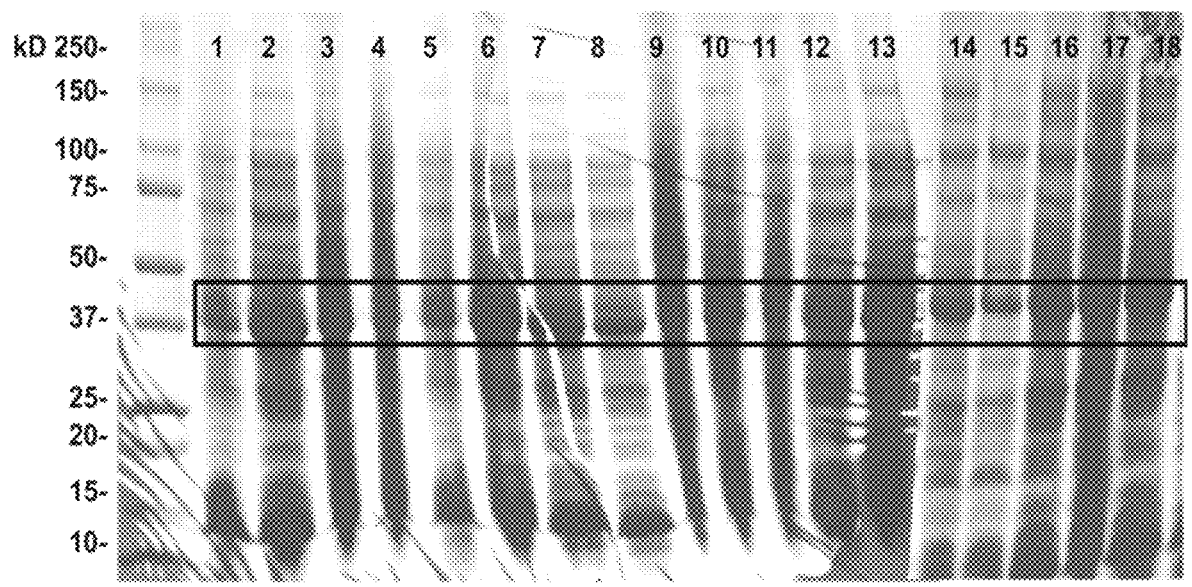
FIG. 3 shows an image of sodium dodecyl sulfate (SDS) electrophoresis gel that shows protein expression by *E. coli* in a BM bioreactor according to an embodiment of the subject invention.
Figure 5:
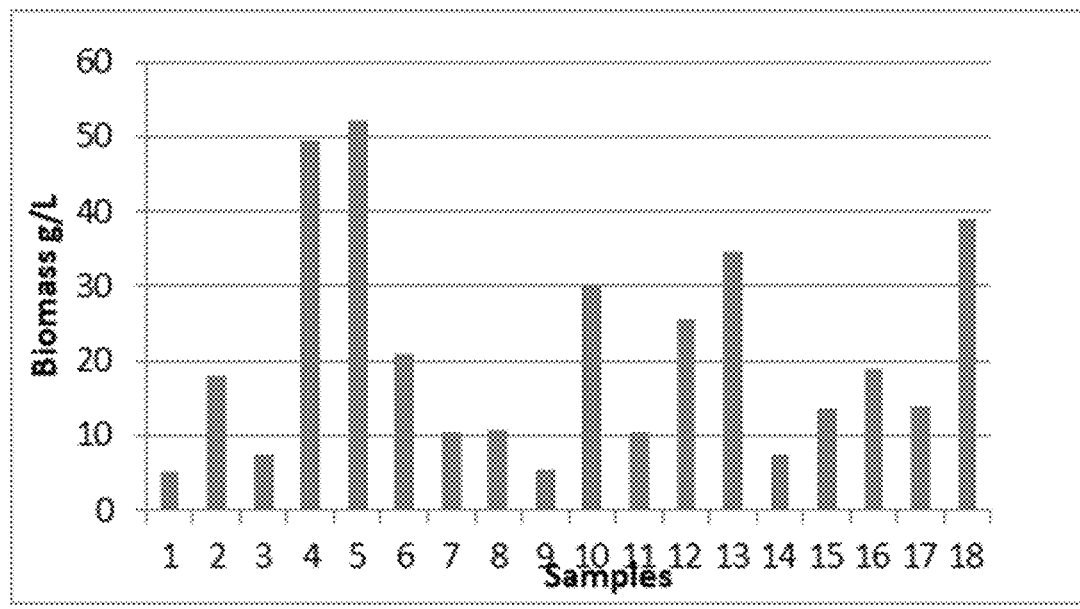
FIG. 5 is a plot of biomass (in grams per liter (g/L) versus sample number, showing *E. coli* biomass produced in a BM bioreactor according to an embodiment of the subject invention, at a continuous flow condition, for each sample.
Figure 6:
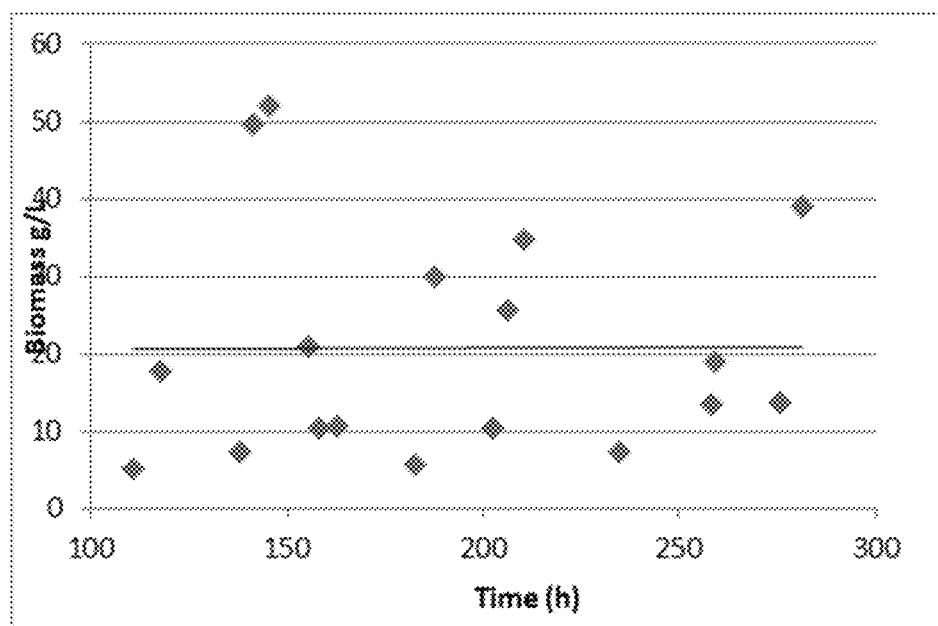
FIG. 6 is a plot of biomass (in g/L) versus time (in h), showing *E. coli* biomass produced in a BM bioreactor according to an embodiment of the subject invention, at a continuous flow condition, at different times.

In order to verify the physiological characteristics of the bacterium and the expression of the recombinant protein in the BM bioreactor, aliquots of the outlet were collected, and the bacterial biomass was calculated (see FIGS. 5 and 6). FIG. 5 is a plot of biomass (in grams per liter (g/L) versus sample number, showing E. coli biomass produced at a continuous flow condition, for each sample; and FIG. 6 is a plot of biomass (in g/L) versus time (in h), showing E. coli biomass produced at a continuous flow condition, at different times. The expression of the protein of interest was observed by an SDS-page protein electrophoresis under denaturing conditions, as shown in FIG. 3.

Figure 7:
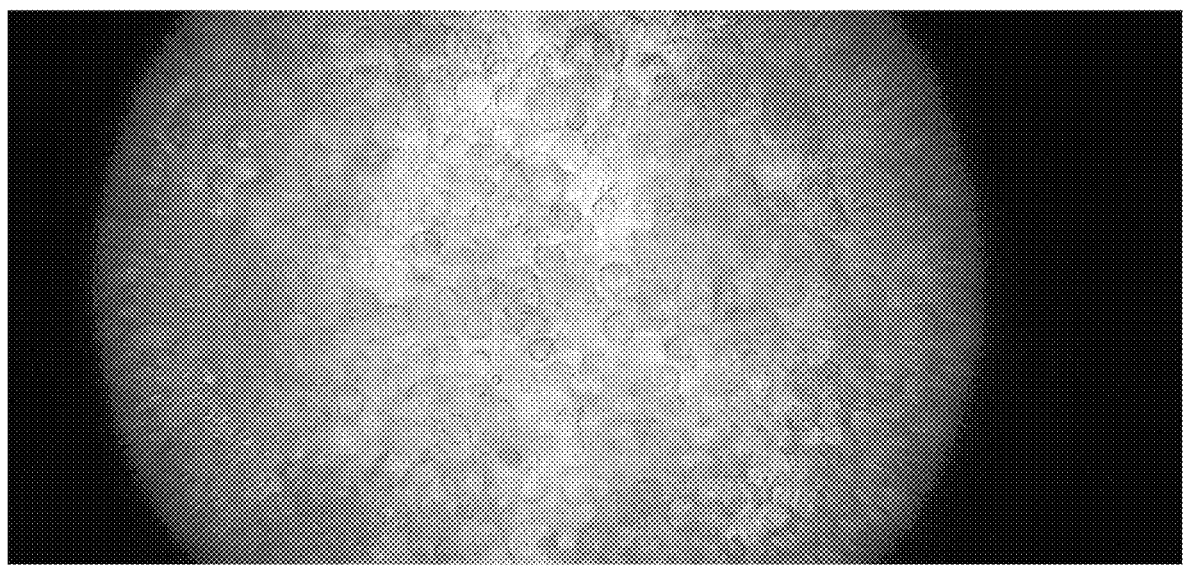
FIG. 7 is a microscopic image showing non-adherent morphology of Chinese hamster ovary (CHO) cells producing monoclonal antibodies grown in a BM bioreactor according to an embodiment of the subject invention at a continuous flow condition.
Figure 8:
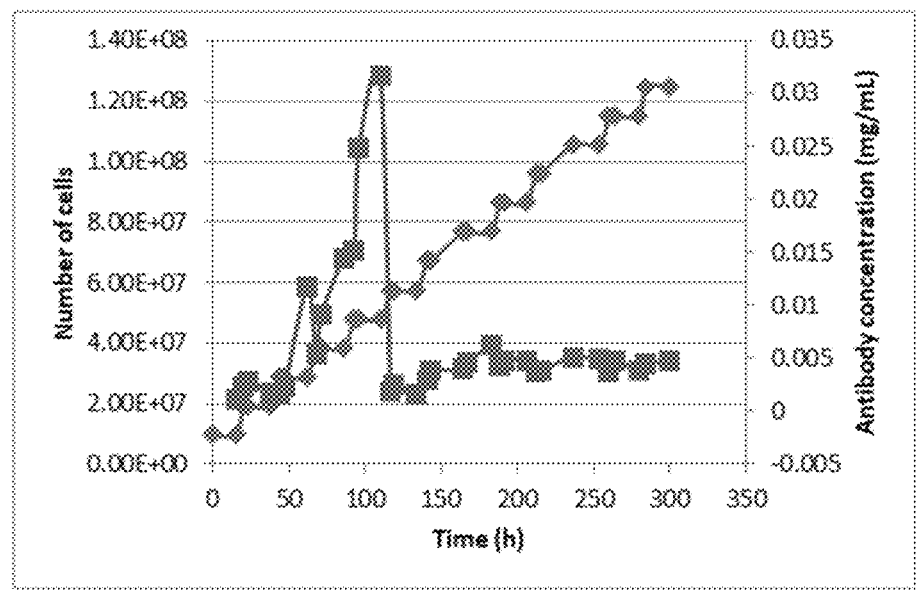
FIG. 8 is a plot of number of cells (left vertical axis) versus time (in h) and antibody concentration (in milligrams per milliliter (mg/ml)) (right vertical axis) versus time (in h), showing production of monoclonal antibodies by CHO cells in a BM bioreactor according to an embodiment of the subject invention at continuous flow. The line that is higher at the right side of the plot is for the number of cells, and the line that is lower at the right side of the plot is for antibody concentration.

In order to evaluate the growth and production of mammalian cells in the BM bioreactor cistern design, non-adherent morphology of Chinese hamster ovary (CHO) cells was cultured and monoclonal antibodies were produced in the BM bioreactor. FIG. 7 shows the ExpiCHO Expression System cells in the microchannels. The BM bioreactor was fed with CHO cells at an initial active concentration that favors the production of monoclonal antibodies, at a continuous flow of 6.38 μL/min. The number of cells and the concentration of monoclonal antibodies in samples taken from the outlet were determined as a function of time (see FIG. 8). The number of cells in the outlet increased as a function of time, which evidences good cell growth in the BM bioreactor. The production of antibodies by CHO cells increased from the initial time to 117 h and then remained constant at an approximate concentration of 0.0051 milligrams per milliliter (mg/ml) until the end of production.

Figure 9:
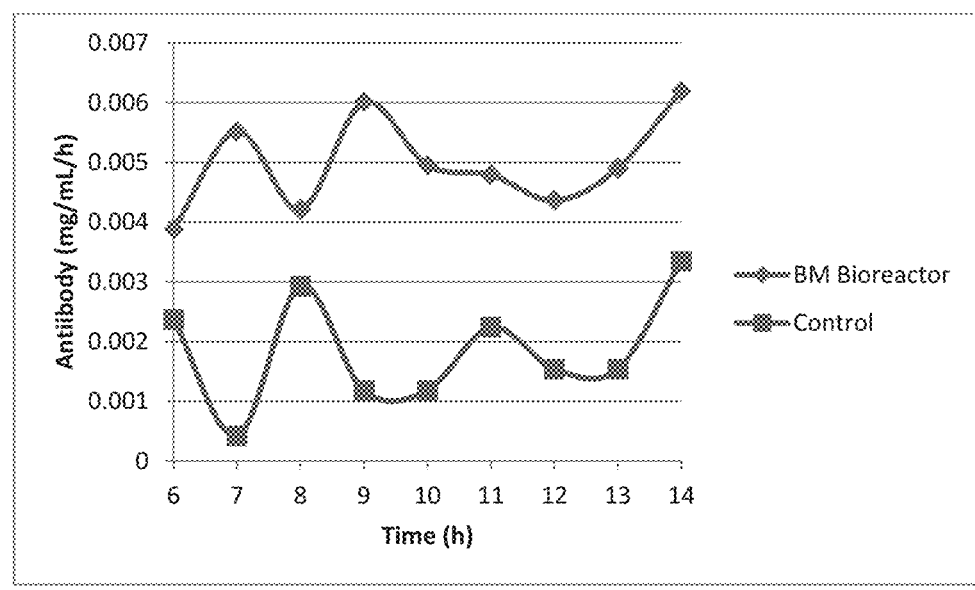
FIG. 9 is a plot of antibody concentration (in mg/ml) versus time (in h), showing production of monoclonal antibodies in a BM bioreactor according to an embodiment of the subject invention at continuous flow, and also in a flask as a control. The uppermost line with the diamond data points if for the BM bioreactor, and the lowermost line with the square data points is for the control in the flask.

FIG. 9 shows the productivity of monoclonal antibodies as a function of time in the BM Bioreactor and in an Erlenmeyer flask as a control. Higher productivity was observed in the bioreactor BM under continuous conditions.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A macro-sized microbioreactor (BM bioreactor) comprising:
    a plurality of microfluidic channels, an area of the BM bioreactor taken up by the plurality of microfluidic channels being at least 20 square inches (in$^2$); and
    a rigid substrate on which the plurality of microfluidic channels is disposed, the substrate being rolled into a cylinder.

2. The BM bioreactor according to claim 1, the area of the BM bioreactor taken up by the plurality of microfluidic channels being at least 2 square meters (m$^2$).

3. The BM bioreactor according to claim 1, the plurality of microfluidic channels being formed of a polymeric material.

4. The BM bioreactor according to claim 3, the BM bioreactor further comprising a rigid substrate on which the polymeric material is irreversibly bonded.

5. The BM bioreactor according to claim 1, the plurality of microfluidic channels being arranged in a cistern pattern.

6. The BM bioreactor according to claim 5, the BM bioreactor further comprising an inlet, an outlet, and a network of symmetrical microchannels with curved corners connecting the inlet to the plurality of microfluidic channels and connecting the outlet to the plurality of microfluidic channels.

7. The BM bioreactor according to claim 1, the BM bioreactor further comprising an inlet, an outlet, and a network of symmetrical microchannels with curved corners connecting the inlet to the plurality of microfluidic channels and connecting the outlet to the plurality of microfluidic channels.

8. The BM bioreactor according to claim 1, further comprising:
    an inlet at a first end of the cylinder and connected to the plurality of microfluidic channels; and
    an outlet at a second end of the cylinder and connected to the plurality of microfluidic channels, the first end being opposite from the second end.

9. The BM bioreactor according to claim 1, further comprising:
    a first polymer layer having the plurality of microfluidic channels; and
    a second polymer layer disposed on the first polymer layer and having additional microfluidic channels.

10. The BM bioreactor according to claim 9, an area of the BM bioreactor taken up by the additional microfluidic channels being at least 20 in$^2$.

11. The BM bioreactor according to claim 10, further comprising a plurality of micropillars disposed between the first polymer layer and the second polymer layer, providing physical separation between the first polymer layer and the second polymer layer.

12. The BM bioreactor according to claim 9, further comprising a plurality of micropillars disposed between the first polymer layer and the second polymer layer, providing physical separation between the first polymer layer and the second polymer layer.

13. A macro-sized microbioreactor (BM bioreactor) comprising:
- a plurality of microfluidic channels, an area of the BM bioreactor taken up by the plurality of microfluidic channels being at least 20 square inches (in$^2$);
- a substrate on which the plurality of microfluidic channels are disposed;
- an inlet at a first end of the substrate and connected to the plurality of microfluidic channels;
- an outlet at a second end of the substrate and connected to the plurality of microfluidic channels, the first end being opposite from the second end;
- a network of symmetrical microchannels with curved corners connecting the inlet to the plurality of microfluidic channels and connecting the outlet to the plurality of microfluidic channels;
- a first polymer layer having the plurality of microfluidic channels;
- a second polymer layer disposed on the first polymer layer and having additional microfluidic channels, an area of the BM bioreactor taken up by the additional microfluidic channels being at least 20 in$^2$; and
- a plurality of micropillars disposed between the first polymer layer and the second polymer layer, providing physical separation between the first polymer layer and the second polymer layer.

14. The BM bioreactor according to claim 13, the area of the BM bioreactor taken up by the plurality of microfluidic channels being at least 2 square meters (m$^2$).

15. The BM bioreactor according to claim 13, the plurality of microfluidic channels being formed of a polymeric material.

16. The BM bioreactor according to claim 15, the substrate being a rigid substrate on which the polymeric material is irreversibly bonded.

17. The BM bioreactor according to claim 13, the plurality of microfluidic channels being arranged in a cistern pattern.

18. A macro-sized microbioreactor (BM bioreactor) comprising:
- a plurality of microfluidic channels, an area of the BM bioreactor taken up by the plurality of microfluidic channels being at least 2 square meters (m$^2$);
- a rigid substrate on which the plurality of microfluidic channels is disposed, the substrate being rolled into a cylinder;
- an inlet at a first end of the cylinder and connected to the plurality of microfluidic channels;
- an outlet at a second end of the cylinder and connected to the plurality of microfluidic channels, the first end being opposite from the second end;
- a first polymer layer having the plurality of microfluidic channels;
- a second polymer layer disposed on the first polymer layer and having additional microfluidic channels, an area of the BM bioreactor taken up by the additional microfluidic channels being at least 20 in$^2$; and
- a plurality of micropillars disposed between the first polymer layer and the second polymer layer, providing physical separation between the first polymer layer and the second polymer layer,
- the first polymer being irreversibly bonded on the rigid substrate,
- the plurality of microfluidic channels being arranged in a cistern pattern, and
- the BM bioreactor further comprising a network of symmetrical microchannels with curved corners connecting the inlet to the plurality of microfluidic channels and connecting the outlet to the plurality of microfluidic channels.

* * * * *